(12) United States Patent
Newell et al.

(10) Patent No.: US 9,073,985 B2
(45) Date of Patent: Jul. 7, 2015

(54) METHODS AND PRODUCTS FOR TREATING PROLIFERATIVE DISEASES

(75) Inventors: Martha Karen Newell, Holland, TX (US); Susannah K. Rogers, Holland, TX (US)

(73) Assignee: The Regents of the University of Colorado, a body corporate, Denver, CO (US)

(*) Notice: Subject to any disclaimer, the term of this patent is extended or adjusted under 35 U.S.C. 154(b) by 684 days.

(21) Appl. No.: 13/054,147

(22) PCT Filed: Jul. 14, 2009

(86) PCT No.: PCT/US2009/004100
§ 371 (c)(1),
(2), (4) Date: Sep. 12, 2011

(87) PCT Pub. No.: WO2010/008554
PCT Pub. Date: Jan. 21, 2010

(65) Prior Publication Data
US 2011/0318335 A1 Dec. 29, 2011

Related U.S. Application Data

(60) Provisional application No. 61/134,799, filed on Jul. 14, 2008, provisional application No. 61/209,439, filed on Mar. 6, 2009.

(51) Int. Cl.
| | | |
|---|---|---|
| *C07K 16/22* | (2006.01) | |
| *A61K 31/4409* | (2006.01) | |
| *A61K 31/7004* | (2006.01) | |
| *A61K 39/395* | (2006.01) | |
| *A61K 45/06* | (2006.01) | |
| *A61K 31/4706* | (2006.01) | |
| *A61K 39/00* | (2006.01) | |

(52) U.S. Cl.
CPC ............ *C07K 16/22* (2013.01); *A61K 31/4409* (2013.01); *A61K 31/7004* (2013.01); *A61K 39/395* (2013.01); *A61K 45/06* (2013.01); *A61K 2039/505* (2013.01); *A61K 31/4706* (2013.01)

(58) Field of Classification Search
None
See application file for complete search history.

(56) References Cited

U.S. PATENT DOCUMENTS

| | | | |
|---|---|---|---|
| 4,724,213 A | 2/1988 | Epstein | |
| 4,818,763 A | 4/1989 | Rusch et al. | |
| 4,935,450 A | 6/1990 | Cone, Jr. | |
| 4,946,866 A | 8/1990 | Wolf et al. | |
| 5,539,132 A | 7/1996 | Royer et al. | |
| 5,585,363 A | 12/1996 | Scanlon et al. | |
| 5,616,554 A | 4/1997 | Beardsley | |
| 5,756,666 A | 5/1998 | Takiguchi et al. | |
| 5,759,837 A | 6/1998 | Kuhajda et al. | |
| 5,766,571 A | 6/1998 | Ceriani et al. | |
| 6,245,904 B1 | 6/2001 | Melms et al. | |
| 6,326,465 B1 | 12/2001 | Hess | |
| 6,416,958 B2 | 7/2002 | Vidovic et al. | |
| 6,670,330 B1 | 12/2003 | Lampidis et al. | |
| 6,979,675 B2 | 12/2005 | Tidmarsh | |
| 7,049,338 B2 | 5/2006 | Ayuko et al. | |
| 7,132,427 B2* | 11/2006 | Wang et al. | 514/266.4 |
| 7,160,865 B2 | 1/2007 | Lampidis et al. | |
| 7,252,829 B1 | 8/2007 | Sette et al. | |
| 7,381,413 B1 | 6/2008 | Newell | |
| 7,390,782 B2 | 6/2008 | Newell | |
| 7,445,794 B1 | 11/2008 | Newell et al. | |
| 7,510,710 B2 | 3/2009 | Newell et al. | |
| 7,816,319 B2 | 10/2010 | Newell | |
| 8,071,645 B2 | 12/2011 | Newell et al. | |
| 8,293,240 B2 | 10/2012 | Newell et al. | |
| 8,329,753 B2 | 12/2012 | Newell et al. | |
| 8,394,377 B2 | 3/2013 | Newell et al. | |
| 2002/0107234 A1 | 8/2002 | Bingham et al. | |
| 2002/0164685 A1 | 11/2002 | Rosen et al. | |
| 2002/0187534 A1 | 12/2002 | Pizer et al. | |
| 2003/0144298 A1 | 7/2003 | Curwen et al. | |
| 2004/0018639 A1 | 1/2004 | Zhabilov | |
| 2004/0116407 A1 | 6/2004 | Borisy et al. | |
| 2004/0167079 A1 | 8/2004 | Tidmarsh | |
| 2004/0180002 A1 | 9/2004 | Young et al. | |
| 2005/0032834 A1* | 2/2005 | Kastan et al. | 514/313 |

(Continued)

FOREIGN PATENT DOCUMENTS

| | | |
|---|---|---|
| CN | 101 920 015 A | 12/2010 |
| WO | WO 95/19765 A1 | 7/1995 |

(Continued)

OTHER PUBLICATIONS

Amaravadi et al. (J. Clin. Invest., 117(2):326-336, 2007).*
Ciardiello et al. (Clinical Cancer Research, 9:1546-1556, 2003).*
Amaravadi et al., Autophagy inhibition enhances therapy-induced apoptosis in a Myc-induced model of lymphoma. J Clin Invest. Feb. 2007;117(2):326-36. Epub Jan. 18, 2007.
Baggetto, Deviant energetic metabolism of glycolytic cancer cells. Biochimie. Nov. 1992;74(11):959-74.
Bell et al., 2-Deoxy-D-glucose preferentially kills multidrug-resistant human KB carcinoma cell lines by apoptosis. Br J Cancer. Dec. 1998;78(11):1464-70.

(Continued)

*Primary Examiner* — Alana Harris Dent
*Assistant Examiner* — Nelson B Moseley, II
(74) *Attorney, Agent, or Firm* — Wolf, Greenfield & Sacks, P.C.

(57) ABSTRACT

Methods and products for treating proliferative diseases, and wounds, using as a pharmacon an autophagy inhibitor, a glycolytic inhibitor, and/or an agent able to alter cellular production of reactive oxygen, or combination thereof, optionally in combination with one or more chemotherapeutic agents. In some embodiments, the invention combines a 4-aminoquinoline, exemplified by chloroquine, with a glycolytic inhibitor, exemplified by 2-deoxy-D-glucose and anti-VEGF antibodies. The systems and methods of the invention may be used to treat drug-resistant or multi-drug resistant cancers.

8 Claims, 18 Drawing Sheets

(56) References Cited

U.S. PATENT DOCUMENTS

| | | |
|---|---|---|
| 2005/0043250 A1 | 2/2005 | Lampidis et al. |
| 2005/0048071 A1 | 3/2005 | Bae |
| 2005/0074882 A1 | 4/2005 | Newell |
| 2005/0148530 A1* | 7/2005 | McSwiggen et al. ............ 514/44 |
| 2005/0158333 A1 | 7/2005 | Newell |
| 2005/0196396 A1* | 9/2005 | Chen et al. ................. 424/145.1 |
| 2005/0202559 A1 | 9/2005 | Pownall |
| 2005/0271676 A1 | 12/2005 | Sette et al. |
| 2006/0008448 A1 | 1/2006 | Xu et al. |
| 2006/0025351 A1 | 2/2006 | Lampidis et al. |
| 2007/0166281 A1* | 7/2007 | Kosak ........................... 424/85.1 |
| 2008/0095798 A1 | 4/2008 | Humphreys et al. |
| 2008/0181864 A1 | 7/2008 | Newell |
| 2008/0182329 A1 | 7/2008 | Newell |
| 2010/0184710 A1 | 7/2010 | Newell et al. |
| 2011/0206755 A1 | 8/2011 | Newell |
| 2011/0318335 A1 | 12/2011 | Newell et al. |
| 2012/0128724 A1 | 5/2012 | Newell |
| 2012/0329733 A1 | 12/2012 | Newell |

FOREIGN PATENT DOCUMENTS

| | | |
|---|---|---|
| WO | WO 01/35978 A1 | 5/2001 |
| WO | WO 03/031643 A2 | 4/2003 |
| WO | WO 2004/062604 A2 | 7/2004 |
| WO | WO 2004/110255 A2 | 12/2004 |
| WO | WO 2006/042062 A2 | 4/2006 |
| WO | WO 2006/078774 A2 | 7/2006 |
| WO | WO 2006/108276 A1 | 10/2006 |
| WO | WO 2012/138708 A1 | 10/2012 |

OTHER PUBLICATIONS

Blask et al., Melatonin inhibition of cancer growth in vivo involves suppression of tumor fatty acid metabolism via melatonin receptor-mediated signal transduction events. Cancer Res. Sep. 15, 1999;59(18):4693-701.

Bui et al., "Cancer's Sweet Tooth," Cancer Cell, vol. 9, Issue 6, Jun. 2006, 419-420.

Conner, Systemic lupus erythematosus; a report on twelve cases treated with quinacrine (atabrine) and chloroquine (aralen). Ann Rheum Dis. Mar. 1957;16(1):76-81.

Dang et al., Oncogenic alterations of metabolism. Trends Biochem Sci. Feb. 1999;24(2):68-72. Review.

Degasperi et al., Role of mitochondria in the immune response to cancer: a central role for Ca2+. J Bioenerg Biomembr. Feb. 2006;38(1):1-10. Epub Jun. 16, 2006.

Denardo et al., Effect of Lym-1radioimmunoconjugate on refractory chronic lymphocytic leukemia.Cancer. Mar. 1, 1994;73(5):1425-32.

Fanciulli et al., Effect of the antitumor drug Ionidamine on glucose metabolism of adriamycin-sensitive and -resistant human breast cancer cells. Oncol Res. 1996;8(3):111-20.

Fantin et al., "Attenuation of LDH-A expression uncovers a link between glycolysis, mitochondrial physiology, and tumor maintenance," Cancer Cell. Jun. 2006;9(6):425-234.

Finstad et al., Effect of n-3 and n-6 fatty acids on proliferation and differentiation of promyelocytic leukemic HL-60 cells. Blood. Dec. 1, 1994;84(11):3799-809.

Fuld et al., Treatment of rheumatoid arthritis with chloroquine. Br Med J. Nov. 15, 1958;2(5106):1199-201.

Halicka et al., 2-Deoxy-D-glucose enhances sensitivity of human histiocytic lymphoma U937 cells to apoptosis induced by tumor necrosis factor. Cancer Res. Jan. 15, 1995;55(2):444-9.

Harper et al., Characterization of a novel metabolic strategy used by drug-resistant tumor cells. FASEB J. Oct. 2002;16(12):1550-7.

Hernlund et al., Potentiation of chemotherapeutic drugs by energy metabolism inhibitors 2-deoxyglucose and etomoxir. Int J Cancer. Jul. 15, 2008;123(2):476-83.

Jenski et al., Omega-3 fatty acid-containing liposomes in cancer therapy. Proc Soc Exp Biol Med. Dec. 1995;210(3):227-33.

Kaplan et al.; "Effects of 2-Deoxyglucose on Drug-Resistant Human Breast Cancer Cells: Toxicity and Magnetic Resonance Spectroscopy Studies of Metabolism"; 1990; Cancer Res.; 50:544-551.

Kovacevic et al., "The role of glutamine oxidation and the purine nucleotide cycle for adaptation of tumour energetics to the transition from the anaerobic to the aerobic state," Biochem J. Jun. 1, 1988; 252(2): 381-386.

Kuhajda et al., Synthesis and antitumor activity of an inhibitor of fatty acid synthase. Proc Natl Acad Sci USA. Mar. 28, 2000;97(7):3450-4.

Lampidis et al., Selective toxicity of rhodamine 123 in carcinoma cells in vitro. Cancer Res. Feb. 1983;43(2):716-20.

Langgut, "Modulation of the Proliferation and Metabolism of Tumor Cells by the Nutrition Factor, Queuine," Endocytobiosis & Cell Res. 11, 233-238 (1996).

Liu, Fatty acid oxidation is a dominant bioenergetic pathway in prostate cancer. Prostate Cancer Prostatic Dis. 2006;9(3):230-4. Epub May 9, 2006.

Liu, H. et al., "Hypersensitization of tumor cells to glycolytic inhibitors," Biochemistry. May 8, 2001; 40(18): 5542-7.

Newell et al., "Studies with glycolysis-deficient cells suggest that production of lactic acid is not the only cause of tumor acidity," 1993, Proc. Natl. Acad. Sci., vol. 90, pp. 1127-1131.

Newell et al., Does the oxidative/glycolytic ratio determine proliferation or death in immunerecognition? Ann N Y Acad Sci. 1999;887:77-82. Review.

Newell et al., The effects of chemotherapeutics on cellular metabolism and cosequent immune recognition. J Immune Based Ther Vaccines. Feb. 2, 2004;2(1):3.

Nirenberg et al., Inhibition of anaerobic glycolysis in Ehrlich ascites tumor cells by 2-deoxy-D-glucose. Cancer Res. Jun. 1958;18(5):518-21.

Nowell et al., Chloroquine affects biosynthesis of Ia molecules by inhibiting dissociation of invariant (gamma) chains from alpha-beta dimers in B cells. J Exp Med. Oct. 1, 1985;162(4):1371-6.

Page et al., Principles of Chemotherapy, Cancer Management: A Multidisciplinary Approach, 7th Ed., 2003, pp. 21-27.

Papaconstantinou et al., The role of glycolysis in the growth of tumorcells. I. Effects of oxamic acid on the metabolism of Ehrlich ascites tumor cells in vitro. J Biol Chem. Feb. 1961;236:278-84.

Pelicano et al., Glycolysis inhibition for anticancer treatment. Oncogene. Aug. 7, 2006;25(34):4633-46.

Pradelli et al., Glycolysis inhibition sensitizes tumor cells to death receptors-induced apoptosis by AMP kinase activation leading to Mcl-1 block in translation. Oncogene. Mar. 18, 2010;29(11):1641-52. Epub Dec. 7, 2009.

Prentki et al., Glycerolipid metabolism and signaling in health and disease. Endocr Rev. Oct. 2008;29(6):647-76. Epub Jul. 7, 2008. Review.

Rose et al., Effects of dietary omega-3 fatty acids on human breast cancer growth and metastases in nude mice. J Natl Cancer Inst. Nov. 3, 1993;85(21):1743-7.

Sattler et al., Glycolytic metabolism and tumour response to fractionated irradiation. Radiother Oncol. Jan. 2010;94(1):102-9. Epub Dec. 28, 2009.

Savarino et al., The anti-HIV-1 activity of chloroquine. J Clin Virol. Feb. 2001;20(3):131-5.

Saydjari et al., 2-Deoxy-D-glucose inhibits the antitumor effects of alpha-difluoromethylornithine on the growth of colon cancer in vivo. Invest New Drugs. Jul. 1989;7(2-3):131-8.

Sonveaux et al., Targeting lactate-fueled respiration selectively killshypoxic tumor cells in mice. J Clin Invest. Dec. 2008;118(12):3930-42. doi:10.1172/JCI36843. Epub Nov. 20, 2008.

Tannock et al., Failure of 2-deoxy-D-glucose and 5-thio-D-glucose to kill hypoxic cells of two murine tumors. Cancer Res. Mar. 1983;43(3):980-3.

Tolomeo et al., Drug resistance and apoptosis in cancer treatment:development of new apoptosis-inducing agents active in drug resistant malignancies. Curr Med Chem Anticancer Agents. May 2002;2(3):387-401.

Tsuruo et al., Molecular targeting therapy of cancer: drug resistance, apoptosis and survival signal. Cancer Sci. Jan. 2003;94(1):15-21.

(56) References Cited

OTHER PUBLICATIONS

Visonneau et al., Conjugated linoleic acid suppresses the growth of human breast adenocarcinoma cells in SCID mice. Anticancer Res. Mar.-Apr. 1997;17(2A):969-73.

Vivi et al., Comparison of action of the anti-neoplastic drug lonidamine on drug-sensitive and drug-resistant human breast cancer cells: 31P and 13C nuclear magnetic resonance studies. Breast Cancer Res Treat. Mar. 1997;43(1):15-25.

Waki et al., Reassessment of FDG uptake in tumor cells: high FDG uptake as a reflection of oxygen-independent glycolysis dominant energy production. Nucl Med Biol. Oct. 1997;24(7):665-70.

Whelan et al., Cancer immunotherapy: an embarrassment of riches? Drug Discov Today. Mar. 15, 2003;8(6):253-8.

Wu, "Control Mechanisms of Glycolysis in Ehrlich Ascites Tumor Cells," J. Biol. Chem. 1965 240:2827-2832.

Yamada et al., Cellular sensitization to cisplatin and carboplatin with decreased removal of platinum-DNA adduct by glucose-regulated stress. Cancer Chemother Pharmacol. 1999;44(1):59-64.

Zhelev et al., Phenothiazines suppress proliferation and induce apoptosis in cultured leukemic cells without any influence on the viability of normal lymphocytes. Phenothiazines and leukemia. Cancer Chemother Pharmacol. Mar. 2004;53(3):267-75. Epub Dec. 9, 2003.

Maycotte et al., Chloroquine sensitizes breast cancer cells to chemotherapy independent of autophagy. Autophagy. Feb. 2012;8:200-12.

Pizer et al., Inhibition of fatty acid synthesis delays disease progression in a xenograft model of ovarian cancer. Cancer Res. Mar. 15, 1996;56(6):1189-93.

\* cited by examiner

Flow Sample Key - PAGE 1

Date: 3M109     By: _____

Experiment: _____

| Sample # | Description | Sample # | Description |
|---|---|---|---|
| 1. | No tx Ns | 26. | |
| 2. | No tx Ns | 27. | |
| 3. | No tx Lyse | 28. | |
| 4. | No tx Lyse | 29. | |
| 5. | Chloro NS | 30. | |
| 6. | Chloro NS | 31. | |
| 7. | Chloro lyse | 32. | |
| 8. | Chloro lyse | 33. | |
| 9. | Avastin NS | 34. | |
| 10. | Avastin NS | 35. | |
| 11. | Avastin Lyse | 36. | |
| 12. | Avastin Lyse | 37. | |
| 13. | Both NS | 38. | |
| 14. | Both NS | 39. | |
| 15. | Both Lysed | 40. | |
| 16. | Both Lysed | 41. | |
| 17. | No tx PIS | 42. | |
| 18. | No tx PIS | 43. | |
| 19. | Chloro PIS | 44. | |
| 20. | Chloro PIS | 45. | |
| 21. | Avastin PIS | 46. | |
| 22. | Avastin PIS | 47. | |
| 23. | Both PIS | 48. | |
| 24. | Both PIS | 49. | |
| 25. | | 50. | |

Fig. 2A

METHODS AND PRODUCTS FOR TREATING PROLIFERATIVE DISEASES

RELATED APPLICATIONS

This application is a National Stage Application of PCT/US2009/004100 which claims priority under 35 U.S.C. §119(e) to U.S. Provisional Application Ser. No. 61/134,799, filed on Jul. 14, 2008 and U.S. Provisional Application Ser. No. 61/209,439, filed on Mar. 6, 2009, each of which is herein incorporated by reference in its entirety.

FIELD OF INVENTION

The field of the invention generally relates to methods and products for treating proliferative diseases, using combinations of compounds to inhibit cellular metabolism.

BACKGROUND

Normal tissue develops, and is maintained by, processes of cell division and cell death. In many diseases, such as cancer, diabetes mellitus Type I, and autoimmune disease, the normal balance between cell division and cell death is disrupted, causing either a rapid growth of unwanted and potentially dangerous cells, and/or a loss of cells essential to maintaining the functions of tissue. Inappropriate cell division or cell death can result in serious life-threatening diseases. Diseases associated with increased cell division include cancer and atherosclerosis. Diseases resulting from increased cell death include AIDS, neurodegenerative diseases (e.g., Alzheimer's disease, Parkinson's disease, amyotrophic lateral sclerosis, retinitis pigmentosa), aplastic anemia, atherosclerosis (e.g., myocardial infarction, stroke, reperfusion injury), and toxin-induced liver disease.

The immune system, a complex organization of cells, tissues and organs, serves to protect us from potential harm. Extraordinary advances in our understanding of the immune system have been made in the last hundred years, especially since the discovery of the T cell and B cell [2-4]. Native T-cells require two signals for activation. These are recognition of antigens in Major Histocompatibility Complex-encoded (MHC) molecules [2], and a co-stimulation signal [5-9] provided by the B7/CD28 family members or other co-stimulatory molecules such as Fas (CD95) [10]. Previously activated T cells can be reactivated by co-stimulation alone [11, 12]. In the absence of activation, T-cells disregard the tissue. If a T cell is activated the consequences can be: 1) destruction of the damaged cells or 2) repair of damaged cells by promoting regeneration either directly or indirectly.

A natural question is: why doesn't the immune system destroy tumor cells as they arise? In fact, there is substantial evidence that the immune system does play an extensive role in suppressing cancer. For example, it is known that people on immune-suppressive therapy have a much higher cancer rate as do people with AIDS [13] and the very young and very old. However, it is also clear that the ability of the immune system to control cancer is not perfect.

Researchers have for many years tried to stimulate the immune system as a therapeutic strategy against cancer [14, 15]. These attempts have generally been ineffective, although there have been some recent successes [16]. There are many reasons for this variability. These include: I) the inability to activate T cells that can destroy the tumor due to the absence of signal one (lack of recognition of the appropriate tumor antigen); 2) the presence of a signal two that results in the production of the wrong cytokines by T cells which may lead to the growth of tumors, or 3) the failure of activated T cells to kill cancerous cells [17].

Anti-cancer agents may work to promote the death of tumor cells in multiple ways. First, these agents may work by direct cytolysis requiring active participation of the tumor cell in the death process [19]. Second, chemotherapeutics may promote the ability of the tumor cell to be recognized by cells of the immune system and to be killed by immune-directed cell death [20]. Third, these agents may work to "rewire" the death inducing receptor/ligand pairs which include Fas and FasL [18, 19, 20]. The second and third possibilities are not mutually exclusive and may work in concert to result in tumor cell death.

Several cell surface proteins have previously been identified as cell death proteins. These proteins are believed to be involved in initiating a signal which instructs the cell to die. Cell death proteins include, for example, Fas/CD95 (Trauth, et al., *Science*, 245:301, 1989), tumor necrosis factor receptors, immune cell receptors such as CD40, OX40, CD27 and 4-1BB (Smith, et al., *Cell*, 76:959, 1994), and RIP (U.S. Pat. No. 5,674,734). These proteins are believed to be important mediators of cell death. These mediators, however, do not always instruct a cell to die. In some cases, these mediators actually instruct a cell to undergo cell division. The intracellular environment, and particularly the status of the proton motor force and the source of fuel for mitochondrial metabolism, determines whether stimulation of the cell death protein will lead to a signal for death or cell division (see, e.g., U.S. patent application Ser. No. 09/277,575, incorporated herein by reference).

Every year at least 6.2 million people die worldwide from cancer [1]. Many cancer patients will be treated by chemotherapy.

For some people this treatment will be effective, but it many cases chemotherapy is not successful, in part because of the development of drug resistance. It is commonly observed in treating cancers, that initial treatments, such as with chemotherapy and/or radiation therapy, are effective to destroy significant numbers of tumor cells, only to leave behind a small number of tumor cells that are resistant to the treatment, which then multiply to form newly detected tumors that are increasingly resistant to treatment as new rounds of therapy are tried. The growing popularity of "cocktails" of chemotherapy drugs has given rise to multidrug resistant ("MDR") tumor cells, which are ever more difficult to destroy. Drug sensitive tumor cells, under the selective pressure of treatment with drugs, develop into drug resistant versions of the same tumor cell type. It is the drug resistant cells that take over, and with each round of chemotherapy the proportion of drug resistant cells to drug sensitive cells increases, to the point where recovery becomes more and more difficult, and eventually the cancer becomes untreatable. Indeed, drug resistance, either acquired or inherent, is the leading cause of death in cancer [21]. Mechanisms which have been suggested to account for drug resistance include over-expression of a multi-drug resistance transporter (pgp-1) [21], failure to express death inducing receptors [21, 22], and a metabolic strategy that may provide protection from a variety of stresses. Because drug resistance is such an important problem, one of the goals of the present invention is to provide methods to overcome this problem. Methods for dealing with MDR tumor cells have been proposed, but without practical, clear clinical success at entirely eliminating such cells and providing a cure for patients with MDR tumors.

Another mechanism that takes part cell death is autophagy, or autophagocytosis, a catabolic process involving the degradation of a cell's own components through the lysosomal machinery; see Carew et al. [23], incorporated herein by reference. A variety of autophagic processes exist, all having in common the degradation of intracellular components via the lysosome. Of interest in autophagy is the role played by a drug well known in treating or protecting against malaria, namely chloroquine or hydrochloroquin. Chloroquine is a 4-aminoquinoline drug having the formula:

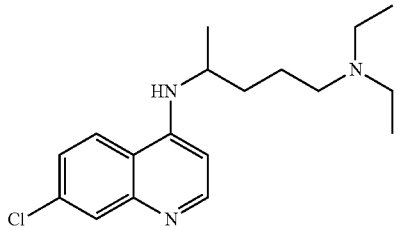 [SMILES: CCN(CC)CCCC(C)Nc1ccnc2cc(Cl)ccc12]

Chloroquine has long been used in the treatment or prevention of malaria. As it also mildly suppresses the immune system, it is used in some autoimmune disorders, such as rheumatoid arthritis and lupus erythematosus. Chloroquine is a lysosomotropic agent, meaning that it accumulates preferentially in the lysosomes of cells in the body. It also has radiosensitizing and chemosensitizing properties, which are beginning to be exploited in anticancer strategies in humans. See in this regard, the following two papers, the disclosures of which are incorporated herein by reference: Savarino A, Lucia M B, Giordano F, Cauda R. "Risks and benefits of chloroquine use in anticancer strategies." Lancet Oncol. 2006 October; 7(10):792-3; and Sotelo J, Briceno E, Lopez-Gonzalez M A. "Adding chloroquine to conventional treatment for glioblastoma multiforme: a randomized, double-blind, placebo-controlled trial." Ann Intern Med. 2006 Mar. 7; 144(5):337-43. Summary for patients in: Ann Intern Med. 2006 Mar. 7; 144(5):131.

SUMMARY OF INVENTION

The invention generally relates to systems and methods for treating proliferative diseases using as a pharmacon an autophagy inhibitor and a glycolytic inhibitor, optionally in combination with one or more chemotherapeutic agents and/or fatty acid metabolism inhibitors. In some embodiments, the invention combines a 4-aminoquinoline as the autophagy modulator, exemplified by chloroquine, with a glycolytic inhibitor, exemplified by a 2-deoxyglucose compound, represented by 2-deoxy-D-glucose or an anti-VEGF antibody.

In one aspect the invention is a method for treating melanoma by administering to a subject a therapeutically acceptable amount of an autophagy inhibitor and an anti-VEGF antibody in an effective amount to treat the melanoma. In one embodiment the anti-VEGF antibody is bevacizumab. In another embodiment the autophagy modulator is a 4-aminoquinoline. For instance, the 4-aminoquinoline may be a chloroquine compound having the formula:

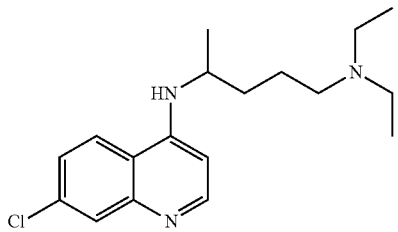 [SMILES: CCN(CC)CCCC(C)Nc1ccnc2cc(Cl)ccc12]

In some embodiments the autophagy inhibitor is chloroquine.

In another aspect the invention is a method for treating melanoma by administering to a subject a therapeutically acceptable amount of an autophagy inhibitor and a glycolytic inhibitor in an effective amount to treat the melanoma. In one embodiment the glycolytic inhibitor is a 2-deoxyglucose compound. In another embodiment the autophagy modulator is chloroquine.

According to yet another aspect of the invention a method for treating a drug resistant tumor is provided. The method involves administering to a subject a therapeutically acceptable amount of an autophagy inhibitor and a glycolytic inhibitor in an effective amount to treat the drug resistant tumor. The drug resistant tumor may be, for instance, a melanoma, an ovarian tumor or a glioblastoma. In some embodiments the subject is further administered an anti-cancer agent. In yet other embodiments the subject is administered a fatty acid metabolism inhibitor.

In other aspects the invention is a method for treating a drug sensitive tumor by administering to a subject a therapeutically acceptable amount of an autophagy inhibitor, a glycolytic inhibitor, and an anti-cancer agent in an effective amount to treat the drug sensitive tumor. The drug resistant tumor may be, for instance, a melanoma, an ovarian tumor or a glioblastoma. In some embodiments the anti-cancer agent is a chemotherapeutic agent. In yet other embodiments the subject is administered a fatty acid metabolism inhibitor.

In other aspects the invention is a method involving determining whether a tumor in a subject has one or more drug resistant cells, administering to the subject a therapeutically acceptable amount of an autophagy inhibitor and a glycolytic inhibitor in conjunction with an anti-cancer agent, if the subject has one or more drug resistant cells. The drug resistant tumor may be, for instance, a melanoma, an ovarian tumor or a glioblastoma. In some embodiments the anti-cancer agent is a chemotherapeutic agent. In yet other embodiments the subject is administered a fatty acid metabolism inhibitor.

A composition is provided according to other aspects of the invention. The composition includes a therapeutically acceptable combination of an autophagy inhibitor and a glycolytic inhibitor, wherein the autophagy inhibitor is not conjugated to the glycolytic inhibitor, and a pharmaceutically acceptable carrier. In some embodiments the pharmaceutically acceptable carrier is sterile. In other embodiments the glycolytic inhibitor is a 2-deoxyglucose compound. In yet other embodiments the 2-deoxyglucose compound has the formula:

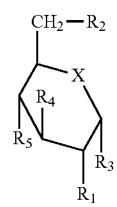

wherein
X represents an O or S atom;
$R_1$ represents a hydrogen atom or a halogen atom;
$R_2$ represents a hydroxyl group, a halogen atom, a thiol group, or CO—$R_6$;
$R_3$, $R_4$, and $R_5$ each represent a hydroxyl group, a halogen atom, or CO—$R_6$,
$R_6$ represents an alkyl group of from 1 to 20 carbon atoms, and
at least two of $R_3$, $R_4$, and $R_5$ are hydroxyl groups.

In one embodiment the 2-deoxyglucose compound is 2-deoxy-D-glucose.

The invention in some aspects is a kit including a container housing an autophagy inhibitor; a container housing an anti-VEGF antibody, and instructions for administering the autophagy inhibitor and the anti-VEGF antibody to a subject having cancer. In some embodiments the anti-VEGF antibody is bevacizumab.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control.

In one set of embodiments of the invention, a cell is exposed to a the compositions of the invention. In another set of embodiments, an immunity profile of a tumor cell is altered by exposing the tumor cell to the compositions of the invention. In another set of embodiments, the method includes an act of administering the compositions of the invention to a subject susceptible to or exhibiting symptoms of drug-resistant cancer, in some cases where the subject is not otherwise indicated for treatment with the compositions of the invention. In another set of embodiments, the method includes an act of administering the compositions of the invention to a subject susceptible to or exhibiting symptoms of cancer, in some cases, where the subject is not otherwise indicated for treatment with the compositions of the invention.

The method, in yet another set of embodiments, includes an act of administering, to a subject susceptible to or exhibiting symptoms of cancer, a therapeutically acceptable amount of the compositions of the invention. The subject, in some cases, may not otherwise be indicated for treatment with the compositions of the invention.

According to another set of embodiments, the method includes an act of administering, to a wound in a subject, a therapeutically acceptable amount of the compositions of the invention.

The method, in yet another set of embodiments, includes acts of surgically removing a tumor from a subject; and inserting the compositions of the invention into the subject. In another set of embodiments, the invention provides an act of inserting the compositions of the invention into or proximate a tumor. The invention, in still another set of embodiments, includes acts of removing cells from a tumor, exposing the cells to the compositions of the invention, and inserting the cells into a subject. In one set of embodiments, the method includes an act of altering an immunity profile of a tumor cell by exposing the tumor cell to the compositions of the invention. In another set of embodiments, the method includes an act of administering the compositions of the invention to a subject having or at risk of developing an autoimmune disease.

In another aspect, the invention provides a composition that includes a cell exposed to the compositions of the invention. In yet another set of embodiments, the invention includes the compositions and a pharmaceutically acceptable carrier.

The invention, in still another aspect, provides a kit. The kit, according to one set of embodiments, includes the compositions of the invention.

In another aspect, the present invention is directed to a method of making one or more other of the embodiments described herein. In yet another aspect, the present invention is directed to a method of using one or more other of the embodiments described herein. In still another aspect, the present invention is directed to a method of promoting one or more other of the embodiments described herein.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control.

BRIEF DESCRIPTION OF THE DRAWINGS

For a more complete understanding of the present invention, reference is now made to the following descriptions taken in conjunction with the accompanying drawing, in which:

FIG. 2A-2M are laboratory pages showing results of the various treatments;

DETAILED DESCRIPTION

Figure 1A:
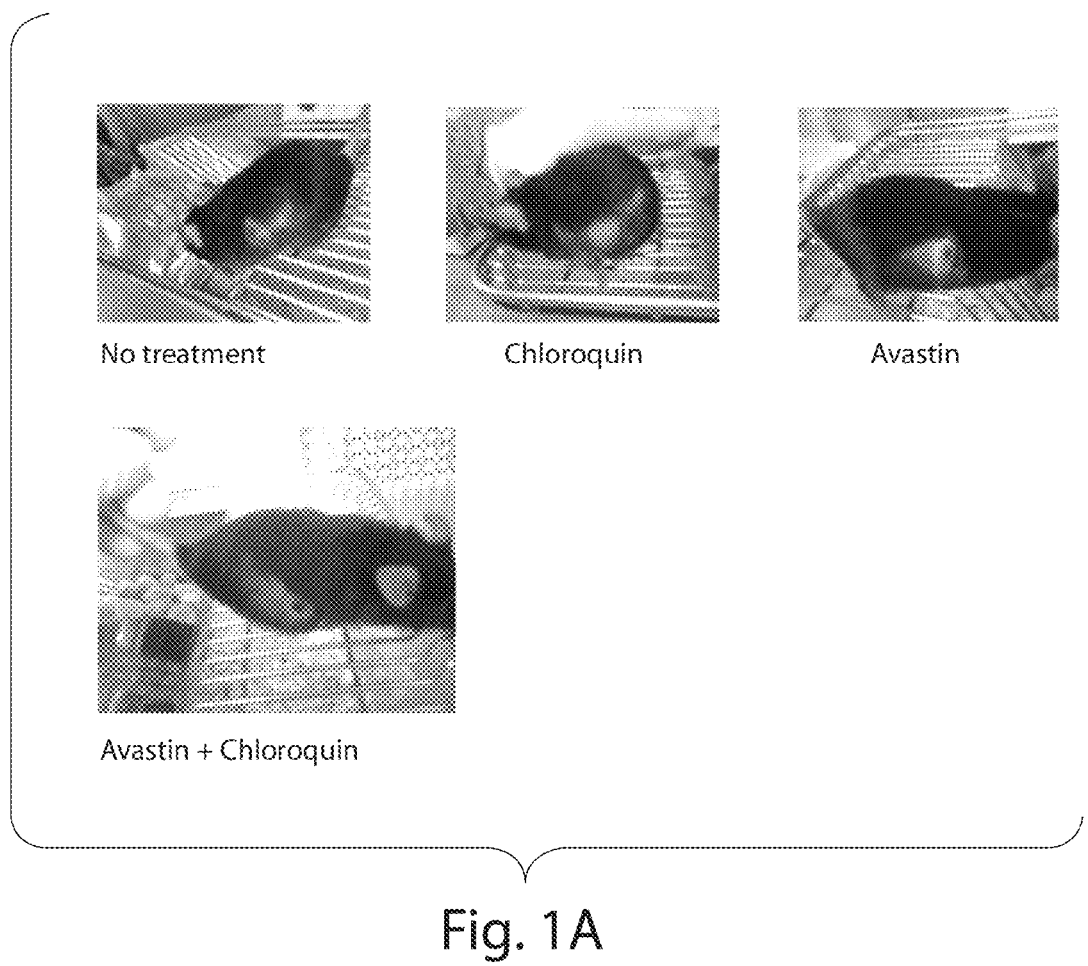
FIG. 1 is a set of photographs sequentially showing the affect on mice with cancerous tumors of no treatment, treatment with chloroquine, treatment with bevacizumab (Avastin®), and treatment with bevacizumab plus chloroquine.

The invention generally relates to methods and products for treating proliferative diseases, using combinations of compounds to block disease-specific cellular metabolic pathways. It is believed that the combinations of compounds of the invention can effectively block multiple cellular metabolic pathways, resulting in cellular apoptosis. For instance, a drug sensitive cell is typically glycolytic, using high rate glycolysis in the cytosol of the cell and high rate glucose oxidation in the mitochondria of the cell for energy generation. Under some conditions drug sensitive cancer cells also use autophagy to generate energy, causing fatty acid accumulation in the lysosome and fatty acid oxidation in the mitochondria. A strategy for killing a drug sensitive cell or causing apoptosis of the cell, according to the invention, would involve the administration of a cocktail of compounds that would block high rate glycolysis and autophagy to cause the cell to remain highly drug sensitive, followed by a traditional anti-proliferative drug. A drug resistant cell depends on lipid metabolism, in specific, fatty acid oxidation, such as that promoted by autophagy, and on high rate glycolysis as a source of energy. Treating a drug resistant cell with cocktail of compounds that would block high rate glycolysis and autophagy results in starvation of the cell followed by cell death. Thus, a strategy for killing a drug resistant cell, according to the invention, would involve the administration of a cocktail of compounds that would block glycolysis and autophagy, optionally, followed by a traditional anti-proliferative drug.

In some instances, it is beneficial also to block fatty acid transport into the mitochondria, which can be achieved by a fatty acid metabolism inhibitor.

Thus, the methods of the invention involve the use of a combination of an autophagy inhibitor and a glycolytic inhibitor to inhibit the proliferation of a proliferative cell. In order to enhance the effect of inhibiting proliferation and causing cell death the method may further include the use of a traditional anti-proliferative drug and/or a fatty acid metabolism inhibitor.

As shown in the in vivo and in vitro data presented in the examples, the combination of an autophagy inhibitor, i.e. chloroquine, and a glycolytic inhibitor, i.e. bevacizumab, had potent anti-tumor effects. The ability to block both metabolic pathways in the tumor cells studied produced enhanced tumor cell death. While 4-aminoquinolines such as chloroquine, have been known for treating malaria, and bevacizumab is known for treating cancer, the enhanced effect of the combination in treating cancer is heretofore unknown and unexpected. The cocktails of compounds described herein provide potent therapeutics in the treatment of proliferative disorders.

In particular embodiments, the compositions of the invention comprise a therapeutically acceptable amount of an autophagy modulator and a glycolytic inhibitor, optionally in combination with one or more other chemotherapeutic agents. In preferred embodiments, the invention combines a 4-aminoquinoline as the autophagy modulator, exemplified by chloroquine, with a glycolytic inhibitor, exemplified by a 2-deoxyglucose compound, represented by 2-deoxy-D-glucose and bevacizumab.

In other particular embodiments, an anti-cancer agent, such as methotrexate, trimetrexate, adriamycin, or taxotere, can also administered to the subject, preferably as part of the same treatment regimen. Similarly, immunotherapies, such as tumor cell vaccines, and biotherapies such as cytokine therapies, are useful for stimulating a specific immune response against a cancer antigen. The procedure can be applied along with or after radiation treatment, and after surgically removing a tumor from the subject.

The present invention generally relates to systems and methods for treating proliferative diseases such as cancers, immunological conditions, autoimmune diseases, and wounds. Various aspects of the invention involve the treatment of cells with an autophagy modulator and a glycolytic inhibitor, optionally in combination with one or more agents and/or fatty acid metabolism inhibitors. The manipulation of the cells may be performed simultaneously or sequentially, in any order. The cells may be manipulated under any suitable condition, i.e., in vivo, ex vivo, in vitro, etc.

Autophagy Modulators

According to one set of embodiments, the cells are exposed to an autophagy modulator. An "autophagy modulator," as used herein, is a lysosomotropic agent, meaning that it accumulates preferentially in the lysosomes of cells in the body. While the mechanism of operation is not well understood by scientists working with autophagy modulators, it appears that such a modulator is effective both to kills cells by increasing autophagy with drug sensitive cells that do not need fatty acid oxidation/autophagy for their metabolic strategies, and by inhibiting autophagy in cells that depend on autophagy to survive. Again, while no one knows exactly how its lysosoma-tropic properties function, it may well inhibit the acidic hydrolases (enzymes in the lysosomes) that are necessary to break down proteins, lipids, etc. for processing and removal) by being attracted to the lysosome and by increasing the pH to decrease the necessary acidity for the enzymes to work.

The autophagy modulator is preferably an autophagy inhibitor. An autophagy inhibitor, as used herein, is any compound which blocks the collection or metabolism of lipids in the lysosome. In some embodiments, the autophagy inhibitor is selected from the group consisting of: chloroquine compounds, 3-methyladenine, bafilomycin A1, 5-amino-4-imidazole carboxamide riboside (AICAR), okadaic acid, autophagy-suppressive algal toxins which inhibit protein phosphatases of type 2A or type 1, analogues of cAMP, and drugs which elevate cAMP levels, adenosine, N6-mercaptopurine riboside, wortmannin, and vinblastine. In addition, antisense or siRNA that inhibit expression of proteins essential for autophagy, such as for example ATG5, may also be used according to the methods of the invention.

The autophagy inhibitor is preferably a chloroquine compound. Chloroquine is a synthetically manufactured drug containing a quinoline nucleus (The Merck Index, p. 2220, 1996). The chloroquine compounds useful according to the invention include chloroquine analogs and derivatives. A number of chloroquine analogs and derivatives are well known. For example, suitable compounds include but are not limited to chloroquine, chloroquine phosphate, hydroxychloroquine, chloroquine diphosphate, chloroquine sulphate, hydroxychloroquine sulphate, or enantiomers, derivatives, analogs, metabolites, pharmaceutically acceptable salts, and mixtures thereof.

Examples of suitable chloroquine compounds include chloroquine phosphate; 7-chloro-4-(4-diethylamino-1-butylamino)quinoline (desmethylchloroquine); 7-hydroxy-4-(4-diethylamino-1-butylamino)quinoline; 7-chloro-4-(1-carboxy-4-diethylamino-1-butylamino)quinoline; 7-hydroxy-4-(1-carboxy-4-diethylamino-1-butylamino)quinoline; 7-chloro-4-(1-carboxy-4-diethylamino-1-methylbutylamino)quinoline; 7-hydroxy-4-(1-carboxy-4-diethylamino-1-methylbutylamino)quinoline; 7-chloro-4-(4-ethyl-(2-hydroxyethyl)-amino-1-methylbutylamino)quinoline (hydroxychloroquine); 7-hydroxy-4-(4-ethyl-(2-hydroxyethyl)-amino-1-methylbutylamino)quinoline; hydroxychloroquine phosphate; 7-chloro-4-(4-ethyl-(2-hydroxyethyl)-amino-1-butylamino)quinoline (desmethylhydroxychloroquine); 7-hydroxy-4-(4-ethyl-(2-hydroxyethyl)-amino-1butylamino)quinoline; 7-chloro-4-(1-carboxy-4-ethyl-(2-hydroxyethyl)-amino-1-butylamino) quinoline; 7-hydroxy-4-(1-carboxy-4-ethyl-(2-hydroxyethyl)-amino-1-butylamino)quinoline; 7-chloro-4-(1-carboxy-4-ethyl-(2-hydroxyethyl)-amino-1-methylbutylamino)quinoline; 7-hydroxy-4-(1-carboxy-4-ethyl-(2-hydroxyethyl)-amino-1-methylbutylamino)-quinoline; 8[(4-aminopentyl)amino]-6-methoxydihydrochloride quinoline; 1-acetyl-1,2,3,4-tetrahydroquinoline; 8-[4-aminopentyl)amino]-6-methoxyquinoline dihydrochloride; 1-butyryl-1,2,3,4-tetrahydroquinoline; 7-chloro-2-(o-chlorostyryl)-4-[4-diethylamino-1-methy[butyl]aminoquinolin-e phosphate; 3-chloro-4-(4-hydroxy-chloroquine, bis(2-methyl-1-pyrrolidinyl)-2,5-x-yl idinoquinoline, 4-[(4-diethylamino)-1-methylbutyl)amino]-6-methoxyquinoline; 3,4-dihydro-1 (2H)-quinolinecarboxyaldehyde; 1,1'-pentamethylenediquinoleinium diiodide; and 8-quinolinol sulfate, enantiomers thereof, as well as suitable pharmaceutical salts thereof.

Chloroquine derivatives include aminoquinoline derivatives and their pharmaceutically acceptable salts such as those described in U.S. Pat. Nos. 5,948,791 and 5,596,002. Suitable examples include (S)—$N_2$-(7-Chloro-quinolin-4-yl)-$N_1$,$N_1$-dimethyl-propane-1,2-diamine; (R)—$N_2$-(7-chloro-quinolin-4-yl)-$N_1$,$N_1$-dimethyl-propane-1,-2-diamine; $N_1$-(7-chloro-quinolin-4-yl)-2, $N_2$, $N_2$-trimethyl-pr-opane-1,2- diamine; N₃-(7-chloro-quinolin-4-yl)-N₁,N₁-diethyl-propane-1,3-diam-ine; (RS)-(7-chloro-quinolin-4-yl)-(1-methyl-piperidin-3-yl)-amine; (RS)-(7-chloro-quinolin-4-yl)-(1-methyl-pyrrolidin-3-yl)-amine; (RS)—N₂-(7-Chloro-quinolin-4-yl)-N₁, N₁-dimethyl-propane-1-,2-diamine; (RS)—N₂-(7-chloro-quinolin-4-yl)-N₁,N₁-diethyl-propane-1,-2-diamine; (S)—N₂-(7-chloro-quinolin-4-yl)-N₁,N₁-diethyl-propane-1,2-diamine; (R)—N₂-(7-chloro-quinolin-4-yl)-N₁,N₁-diethyl-propane-1,2-diamine; (RS)-7-chloro-quinolin-4-yl)-(1-methyl-2-pyrrolidin-1-yl-ethyl)-amine; N₂-(7-chloro-quinolin-4-yl)-N₁,N₁-dimethyl-ethane-1,-2-diamine; N₂-(7-chloro-quinolin-4-yl)-N₁-diethyl-ethane-1,2-diamine; N₃-(7-chloro-quinolin-4-yl)-N₁,N₁-dimethyl-propane-1,3-dia-mine; (R)—N₁-(7-chloro-quinolin-4-yl)-N₂, N₂-dimethyl-propa-ne-1,2-diamine; (S)—N₁-(7-chloro-quinoline-4-yl)-N₂, N₂-dimethyl-propane-1-,2-diamine; (RS)-(7-chloro-quinolin-4-yl)-(1-methyl-pyrrolidin-2-yl-methyl)-amine; N₁-(7-Chloro-quinolin-4-yl)-N₂-(3-chloro-benzyl)-2-methyl-propa-ne-1,2-diamine; N₁-(7-chloro-quinolin-4-yl)-N₂-(benzyl)-2-methyl-propane-1,2-di-amine; N₁-(7-chloro-quinolin-4-yl)-N₂-(2-hydroxy-3-methoxy-benzy-1)-2-methyl-propane-1,2-diamine; N₁-(7-chloro-quinolin-4-yl)-N₂-(2-hydroxy-5-methoxy-benzyl)-2-m-ethyl-propane-1,2-diamine; and N₁-(7-chloro-quinolin-4-yl)-N₂-(4-hydroxy-3-methoxy-benzyl)-2-m-ethyl-propane-1,2-diamine; (1S,2S)—N₁-(7-chloro-quinolin-4-yl)-N₂-(benzyl)-cyclohexane-1,-2-diamine; (1S,2S)—N₁-(7-chloro-quinolin-4-yl)-N₂-(4-chlorobenz-yl)-cyclohexane-1,2-diamine; (1S,2S)—N₁-(7-chloro-quinolin-4-yl)-N₂-(4-dimethylamino-benzyl-)-cyclohexane-1,2-diamine; cis-N₁-(7-chloro-quinolin-4-yl)-N₄-(4-dimethylamino-benzyl)-cyc-lohexane-1,4-diamine; cis-N₁-(7-chloro-quinolin-4-yl)-N₄-(benzyl)-cyclohexane-1,4-dia-mine; cis-N₁-(7-chloro-quinolin-4-yl)-N₄-(3-chloro-benzyl)-cyclohexane-1,4-diamine; cis-N₁-(7-chloro-quinolin-4-yl)-N₄-(2-hydroxy-4-methoxy-benzyl)-cyclohexane-1,4-diamine; cis-N₁-(7-chloro-quinolin-4-yl)-N₄-(3,5-dimethoxy-benzyl)-cyclohexane-1,4-diamine; cis-N₁-(7-chloro-quinolin-4-yl)-N₄-(4-methylsulphanyl-benzyl)-cyclohexane-1,4-diamine; cis-N₁-(7-chloro-quinolin-4-yl)-N₄-(4-diethylamino-ben-zyl)-cyclohexane-1,4-diamine; cis-N₁-(7-chloro-quinolin-4-yl)-N₄-(biphenyl-4-yl)methyl-cyclohexane-1,4-diamine; trans-N₁-(7-chloro-quinolin-4-yl)-N₄-[2-(3,5-dimethoxy-phenyl)-ethyl]-cyclohexane-1,4-diamine; cis-N₁-(7-chloro-quinolin-4-yl)-N₄-(4-methoxy-benzyl)-cyclohexane-1,4-di-amine; trans-N₁-(7-chloro-quinolin-4-yl)-N₄-(4-dimethylamino-benzyl)-c-yclohexane-1,4-diamine; and trans-N₁-(7-chloro-quinolin-4-yl)-N₄-(2,6-difluoro-benzyl)-cycl-ohexane-1,4-diamine.

Chloroquine and hydroxychloroquine are generally racemic mixtures of (−)- and (+)-enantiomers. The (−)-enantiomers are also known as (R)-enantiomers (physical rotation) and l-enantiomers (optical rotation). The (+)-enantiomers are also known as (S)-enantiomers (physical rotation) and r-enantiomers (optical rotation). Preferably, the (−)-enantiomer of chloroquine is used. The enantiomers of chloroquine and hydroxychloroquine can be prepared by procedures known to the art.

The compounds of the invention, such as, chloroquine may exhibit the phenomena of tautomerism, conformational isomerism, geometric isomerism, and/or optical isomerism. The invention covers any tautomeric, conformational isomeric, optical isomeric and/or geometric isomeric forms of the compounds described herein, as well as mixtures of these various different forms.

Chloroquine has the formula:

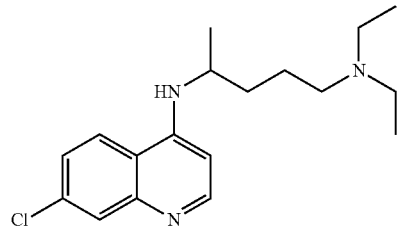 [SMILES: CCN(CC)CCCC(C)Nc1ccnc2cc(Cl)ccc12]

Other examples of preferred chloroquine compounds that can be used in the invention include chloroquine diphosphate and hydroxychloroquine (Plaquenil™).

Glycolytic Inhibitor

Glycolytic inhibitors, as used herein, refer to compounds that inhibit (e.g. slow down or block) the glycolytic pathway within a cell. Glycolytic inhibitors include but are not limited to 2-deoxyglucose compounds and anti-VEGF compounds.

2-deoxyglucose compounds are defined herein as 2-deoxy-D-glucose, and homologs, analogs, and/or derivatives of 2-deoxy-D-glucose. While the levo form is not prevalent, and 2-deoxy-D-glucose is preferred, the term "2-deoxyglucose" is intended to cover inter alia either 2-deoxy-D-glucose and 2-deoxy-L-glucose, or a mixture thereof. In general glycolytic inhibitors can have the formula:

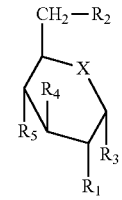

wherein: X represents an O or S atom; $R_1$ represents a hydrogen atom or a halogen atom; $R_2$ represents a hydroxyl group, a halogen atom, a thiol group, or CO—$R_6$; and $R_3$, $R_4$, and $R_5$ each represent a hydroxyl group, a halogen atom, or CO—$R_6$ wherein $R_6$ represents an alkyl group of from 1 to 20 carbon atoms, and wherein at least two of $R_3$, $R_4$, and $R_5$ are hydroxyl groups. The halogen atom is as described above with respect to the oxirane carboxylic acid compounds, and in $R_2$, $R_3$, $R_4$, and $R_5$. The halogen atom is preferably F, and $R_6$ is preferably a $C_3$-$C_{15}$ alkyl group.

Examples of 2-deoxyglucose compounds useful in the invention are: 2-deoxy-D-glucose, 2-deoxy-L-glucose; 2-bromo-D-glucose, 2-fluoro-D-glucose, 2-iodo-D-glucose, 6-fluoro-D-glucose, 6-thio-D-glucose, 7-glucosyl fluoride, 3-fluoro-D-glucose, 4-fluoro-D-glucose, 1-O-propyl ester of 2-deoxy-D-glucose, 1-O-tridecyl ester of 2-deoxy-D-glucose, 1-O-pentadecyl ester of 2-deoxy-D-glucose, 3-O-propyl ester of 2-deoxy-D-glucose, 3-O-tridecyl ester of 2-deoxy-D-glucose, 3-O-pentadecyl ester of 2-deoxy-D-glucose, 4-O-propyl ester of 2-deoxy-D-glucose, 4-O-tridecyl ester of 2-deoxy-D-glucose, 4-O-pentadecyl ester of 2-deoxy-D-glucose, 6-O-propyl ester of 2-deoxy-D-glucose, 6-O-tridecyl ester of 2-deoxy-D-glucose, 6-O-pentadecyl ester of 2-deoxy-D-glucose, and 5-thio-D-glucose, and mixtures thereof.

A preferred glycolytic inhibitor is 2-deoxy-D-glucose, which has the structure:

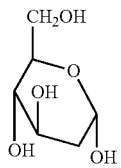

Anti-VEGF compounds, as used herein, refer to compounds that reduce VEGF signaling. Anti-VEGF compounds are VEGF antagonists, including but not limited to anti-VEGF antibodies, anti-VEGF receptor antibodies, VEGF antisense, VEGF siRNA etc.

The term "VEGF" refers to the vascular endothelial cell growth factor, as described by Leung et al. Science, 246:1306 (1989), and Houck et al. Mol. Endocrin., 5:1806 (1991), together with the naturally occurring allelic and processed forms thereof. The term "VEGF" is also used to refer to known truncated forms of the polypeptide.

A "VEGF antagonist" refers to a molecule capable of neutralizing, blocking, inhibiting, abrogating, reducing or interfering with VEGF activities including its binding to one or more VEGF receptors. VEGF antagonists include anti-VEGF antibodies and antigen-binding fragments thereof, receptor molecules and derivatives which bind specifically to VEGF thereby sequestering its binding to one or more receptors, anti-VEGF receptor antibodies and VEGF receptor antagonists such as small molecule inhibitors of the VEGFR tyrosine kinases.

An "anti-VEGF antibody" is an antibody that binds to VEGF with sufficient affinity and specificity to prevent VEGF from interacting with VEGF receptor. An "anti-VEGF receptor antibody" is an antibody that binds to VEGF receptor with sufficient affinity and specificity to block VEGF signaling. Preferably, the anti-VEGF antibody of the invention can be used as a therapeutic agent in targeting and interfering with diseases or conditions wherein the VEGF activity is involved. An anti-VEGF antibody will usually not bind to other VEGF homologues such as VEGF-B or VEGF-C, nor other growth factors such as PlGF, PDGF or bFGF. A preferred anti-VEGF antibody is a recombinant humanized anti-VEGF monoclonal antibody generated according to Presta et al. (1997) Cancer Res. 57:4593-4599, including but not limited to the antibody known as bevacizumab (Avastin®).

Bevacizumab is a major drug developed for treating cancer, including metastatic cancer, and has the trade name Avastin®, by Genentech/Roche. Bevacizumab is a humanized monoclonal antibody, and was the first commercially available angiogenesis inhibitor. It stops tumor growth by preventing the formation of new blood vessels (angiogenesis) by targeting and inhibiting the function of a natural protein called vascular endothelial growth factor that stimulates new blood vessel formation. The drug was first developed as a genetically engineered version of a mouse antibody that contains both human and mouse components, a monoclonal antibody against VEGF-A.

In some embodiments the VEGF antibody is not VEGFR-3 mAb disclosed by Imclone Systems Inc., New York, N.Y.

The term "antibody" herein is used in the broadest sense and specifically covers intact monoclonal antibodies, polyclonal antibodies, multispecific antibodies (e.g. bispecific antibodies) formed from at least two intact antibodies, antibody fragments, so long as they exhibit the desired biological activity, and antibody like molecules such as scFv. A native antibody usually refers to heterotetrameric glycoproteins composed of two identical light (L) chains and two identical heavy (H) chains. Each heavy and light chain has regularly spaced intrachain disulfide bridges. Each heavy chain has at one end a variable domain (VH) followed by a number of constant domains. Each light chain has a variable domain at one end (VL) and a constant domain at its other end; the constant domain of the light chain is aligned with the first constant domain of the heavy chain, and the light-chain variable domain is aligned with the variable domain of the heavy chain. Particular amino acid residues are believed to form an interface between the light- and heavy-chain variable domains.

Numerous VEGF and VEGF receptor antibodies are available commercially for research purposes. Certain portions of the variable domains differ extensively in sequence among antibodies and are used in the binding and specificity of each particular antibody for its particular antigen. However, the variability is not evenly distributed throughout the variable domains of antibodies. It is concentrated in three or four segments called "complementarity-determining regions" (CDRs) or "hypervariable regions" in both in the light-chain and the heavy-chain variable domains. The more highly conserved portions of variable domains are called the framework (FR). The variable domains of native heavy and light chains each comprise four or five FR regions, largely adopting a n-sheet configuration, connected by the CDRs, which form loops connecting, and in some cases forming part of, the β-sheet structure. The CDRs in each chain are held together in close proximity by the FR regions and, with the CDRs from the other chain, contribute to the formation of the antigen-binding site of antibodies (see Kabat et al., NIH Publ. No. 91-3242, Vol. I, pages 647-669 (1991)). The constant domains are not necessarily involved directly in binding an antibody to an antigen, but exhibit various effector functions, such as participation of the antibody in antibody-dependent cellular toxicity.

A hypervariable region or CDR as used herein defines a subregion within the variable region of extreme sequence variability of the antibody, which form the antigen-binding site and are the main determinants of antigen specificity. According to one definition, they can be residues (Kabat nomenclature) 24-34 (L1), 50-56 (L2) and 89-97 (L3) in the light chain variable region and residues (Kabat nomenclature 31-35 (H1), 50-65 (H2), 95-102 (H3) in the heavy chain variable region. Kabat et al., Sequences of Proteins of Immunological Interest, 5th Ed. Public Health Service, National Institute of Health, Bethesda, Md. [1991]).

An "intact" antibody is one which comprises an antigen-binding variable region as well as a light chain constant domain ($C_L$) and heavy chain constant domains, $C_{H1}$, $C_{H2}$ and $C_{H3}$. The constant domains may be native sequence constant domains (e.g. human native sequence constant domains) or amino acid sequence variant thereof. Preferably, the intact antibody has one or more effector functions.

Various techniques have been developed for the production of antibody fragments. Traditionally, these fragments were derived via proteolytic digestion of intact antibodies (see, e.g., Morimoto et al., Journal of Biochemical and Biophysical Methods 24:107-117 (1992); and Brennan et al., Science, 229:81 (1985)). However, these fragments can now be produced directly by recombinant host cells. For example, the antibody fragments can be isolated from antibody phage libraries. Alternatively, Fab'-SH fragments can be directly recovered from *E. coli* and chemically coupled to form F(ab')$_2$ fragments (Carter et al., Bio/Technology 10:163-167

(1992)). According to another approach, F(ab')$_2$ fragments can be isolated directly from recombinant host cell culture.

"Antibody fragments" comprise a portion of an intact antibody, preferably the antigen binding or variable region of the intact antibody. Examples of antibody fragments include Fab, Fab', F(ab')$_2$, and Fv fragments; diabodies; single-chain antibody molecules; and multispecific antibodies formed from antibody fragments. Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')$_2$ fragment that has two antigen-combining sites and is still capable of cross-linking antigen.

"Fv" is the minimum antibody fragment which contains a complete antigen-recognition and -binding site. This region consists of a dimer of one heavy- and one light-chain variable domain in tight, non-covalent association. It is in this configuration that the three CDRs of each variable domain interact to define an antigen-binding site on the surface of the VH-VL dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The Fab fragment also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The term "Fc region" is used to define the C-terminal region of an immunoglobulin heavy chain which may be generated by papain digestion of an intact antibody. The Fc region may be a native sequence Fc region or a variant Fc region. Although the boundaries of the Fc region of an immunoglobulin heavy chain might vary, the human IgG heavy chain Fc region is usually defined to stretch from an amino acid residue at about position Cys226, or from about position Pro230, to the carboxyl-terminus of the Fc region. The Fc region of an immunoglobulin generally comprises two constant domains, a CH2 domain and a CH3 domain, and optionally comprises a CH4 domain. By "Fc region chain" herein is meant one of the two polypeptide chains of an Fc region.

The "hinge region," and variations thereof, as used herein, includes the meaning known in the art, which is illustrated in, for example, Janeway et al., Immuno Biology: the immune system in health and disease, (Elsevier Science Ltd., NY) (4th ed., 1999)

Depending on the amino acid sequence of the constant domain of their heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA, and IgA2. The heavy-chain constant domains that correspond to the different classes of immunoglobulins are called $\alpha$, $\delta$, $\epsilon$, $\gamma$, and $\mu$, respectively. The subunit structures and three-dimensional configurations of different classes of immunoglobulins are well known.

The "light chains" of antibodies (immunoglobulins) from any vertebrate species can be assigned to one of two clearly distinct types, called kappa (K) and lambda ($\lambda$), based on the amino acid sequences of their constant domains.

Fatty Acid Metabolism Inhibitors

According to one set of embodiments, the cells are exposed to a fatty acid metabolism inhibitor. A "fatty acid metabolism inhibitor," as used herein, is a compound able to inhibit (e.g., prevent, or at least decrease or inhibit the activity by an order of magnitude or more) a reaction within the fatty acid metabolism pathway, such as an enzyme-catalyzed reaction within the pathway. The inhibitor may inhibit the enzyme, e.g., by binding to the enzyme or otherwise interfering with operation of the enzyme (for example, by blocking an active site or a docking site, altering the configuration of the enzyme, competing with an enzyme substrate for the active site of an enzyme, etc.), and/or by reacting with a coenzyme, cofactor, etc. necessary for the enzyme to react with a substrate. The fatty acid metabolism pathway is the pathway by which fatty acids are metabolized within a cell for energy (e.g., through the synthesis of ATP and the breakdown of fatty acids into simpler structures, such as $CO_2$, acyl groups, etc.).

The fatty acid metabolism pathway includes several enzymatic reactions, which use various enzymes such as reductases or isomerases. Specific examples of enzymes within the fatty acid metabolism pathway include 2,4-dienoyl-CoA reductase, 2,4-dienoyl-CoA isomerase, butyryl dehydrogenase, etc, as further discussed below. In one embodiment, the fatty acid metabolism inhibitor is an inhibitor able to inhibit a beta-oxidation reaction in the fatty acid metabolism pathway. In another embodiment, the inhibitor is an inhibitor for a fatty acid transporter (e.g., a transporter that transports fatty acids into the cell, or from the cytoplasm into the mitochondria for metabolism). In yet another embodiment, the inhibitor may react or otherwise inhibit key steps within the fatty acid metabolism pathway. In still another embodiment, the inhibitor may be an inhibitor of fatty acids as a source of energy in the mitochondria. For example, the inhibitor may inhibit the breakdown of intermediates such as butyryl CoA, glutaryl CoA, or isovaleryl CoA.

2,4-dienoyl-CoA reductase is an enzyme within the fatty acid metabolism pathway that catalyzes reduction reactions involved in the metabolism of polyunsaturated fatty acids. Certain fatty acids are substrates for 2,4-dienoyl-CoA reductases located within the mitochondria. In some cases, fatty acids may be transported into the mitochondria through uncoupling proteins. The uncoupling protein may, in certain instances, increase the mitochondrial metabolism to increase the availability of fatty acids within the mitochondria and/or increase the throughput of beta-oxidation within the mitochondria.

The enzyme 2,4-dienoyl-CoA isomerase is an enzyme within the fatty acid metabolism pathway that catalyzes isomerization of certain fatty acids. One step in the metabolism of certain polyunsaturated fatty acids may be protective against reactive oxygen intermediates ("ROI"). Thus, by generating substrates and antagonists for the activity of 2,4-dienyol-CoA isomerase, the metabolic production of reactive oxygen intermediates may be enhanced and/or reduced. This, in turn, may affect certain disease states, such as cancer.

Thus, it is to be understood that, as used herein, compounds useful for inhibiting fatty acid metabolism (i.e., "fatty acid metabolism inhibitors") are also useful for altering cellular production of reactive oxygen; compounds described in reference to fatty acid metabolism inhibition should also be understood herein to be able to alter reactive oxygen production within a cell. For example, by altering the ability of a cell to metabolize a fatty acid, the ability of the cell to produce reactive oxygen may also be affected, since one pathway for a cell to produce reactive oxygen intermediates is through the metabolism of fatty acids. Alteration of the production of reactive oxygen in a cell may be associated with changes in the immune profile of cells, i.e., how immune cells respond to the cell. Thus, in some cases, the production of reactive oxygen can be affected by exposing a cell to, or removing a cell from, a fatty acid metabolism inhibitor. The alteration of the production of reactive oxygen may be useful in treating conditions such as cancers or wounds (as further discussed below), as the alteration of the immune profile of cells within the cancer site or the wound may stimulate the immune system and/or other wound-healing processes.

In a preferred embodiment of the invention, the fatty acid inhibitor is an oxirane carboxylic acid compound. In accordance with a discovery of this invention, such compounds, exemplified by etomoxir, are able to alter cellular production of reactive oxygen. Preferred oxirane carboxylic acid compounds have the formula:

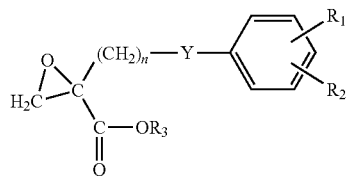

wherein: $R_1$ represents a hydrogen atom, a halogen atom, a 1-4C alkyl group, a 1-4C alkoxy group, a nitro group or a trifluoromethyl group; $R_2$ has one of the meanings of $R_1$; $R_3$ represents a hydrogen atom or a 1-4C alkyl group; Y represents the grouping —O—$(CH_2)_m$—; m is 0 or a whole number from 1 to 4; and n is a whole number from 2 to 8 wherein the sum of m and n is a whole number from 2 to 8. More preferred are oxirane carboxylic acid compounds wherein $R_1$ is a halogen atom, $R_2$ is a hydrogen atom, m is 0, and n is 6, and more particularly where $R_3$ is an ethyl group.

It is most particularly preferred to use etomoxir, i.e., 2-(6-(4-chlorophenoxy)-hexyl)-oxirane-2-carboxylic acid ethyl ester. Examples of other oxirane carboxylic acid compounds useful in the invention are 2-(4-(3-chlorophenoxy)-butyl)-oxirane-2-carboxylic acid ethyl ester, 2-(4-(3-trifluoromethylphenoxy)-butyl)-oxirane-2-carboxylic acid ethyl ester, 2-(5 (4-chlorophenoxy)-pentyl)-oxirane-2-carboxylic acid ethyl ester, 2-(6-(3,4-dichlorophenoxy)-hexyl)-oxirane-2-carboxylic acid ethyl ester, 2-(6-(4-fluorophenoxy)-hexyl)-oxirane-2-carboxylic acid ethyl ester, and 2-(6-phenoxyhexyl)-oxirane-2-carboxylic acid ethyl ester, the corresponding oxirane carboxylic acids, and their pharmacologically acceptable salts.

The foregoing class of oxirane carboxylic acid compounds, including etomoxir, has been described by Horst Wolf and Klaus Eistetter in U.S. Pat. No. 4,946,866 for the prevention and treatment of illnesses associated with increased cholesterol and/or triglyceride concentration, and by Horst Wolf in U.S. Pat. No. 5,739,159 for treating heart insufficiency. The preparation of oxirane carboxylic acid compounds, and their use for blood glucose lowering effects as an antidiabetic agent, is described in Jew et al U.S. Pat. No. 6,013,666. Etomoxir has been described as an inhibitor of mitochondrial carnitine palmitoyl transferase-I by Mannaerts, G. P., L. J. Debeer, J. Thomas, and P. J. De Schepper "Mitochondrial and peroxisomal fatty acid oxidation in liver homogenates and isolated hepatocytes from control and clofibrate-treated rats," J. Biol. Chem. 254:4585-4595, 1979. U.S. Patent Application 20030036199 by Bamdad et al, entitled: "Diagnostic tumor markers, drug screening for tumorigenesis inhibition, and compositions and methods for treatment of cancer", published Feb. 20, 2003, describes treating a subject having a cancer characterized by the aberrant expression of MUC 1, comprising administering to the subject etomoxir in an amount effective to reduce tumor growth. In a preferred aspect of this embodiment, subjects for whom the methods of the invention involving treatment with etomoxir are not intended are those diagnosed with diseases which already call for treatment with etomoxir, particularly those subjects who have MUC 1-dependant tumors, nor those diagnosed with diabetes, or diseases associated with increased cholesterol and/or triglyceride concentration, or chronic heart failure (e.g., failing cardiac hypertrophy associated with an inadequate sarcoplasmic reticulum function) calling for treatment with etomoxir.

The foregoing U.S. Pat. Nos. 4,946,866, 5,739,159, and 6,013,666, U.S. Patent Application 20030036199, and the foregoing publication by Mannaerts, G. P., L. J. Debeer, J. Thomas, and P. J. De Schepper, are incorporated herein by reference. In addition, U.S. patent application Ser. No. 10/272,432, filed Oct. 15, 2002, entitled "Methods for Regulating Co-Stimulatory Molecule Expression with Reactive Oxygen," by M. K. Newell, et al. is incorporated herein by reference in its entirety.

In a specific embodiment, the method includes the step of administering, to a subject susceptible to or exhibiting symptoms of cancer, preferably a subject susceptible to or exhibiting symptoms of drug-resistant cancer, a therapeutically acceptable amount of the oxirane carboxylic acid compound, exemplified by etomoxir. A "subject," as used herein, means a human or non-human mammal, the latter including, but not limited to, a dog, cat, horse, cow, pig, sheep, goat, chicken, primate, rat, and mouse.

Figure 1B:
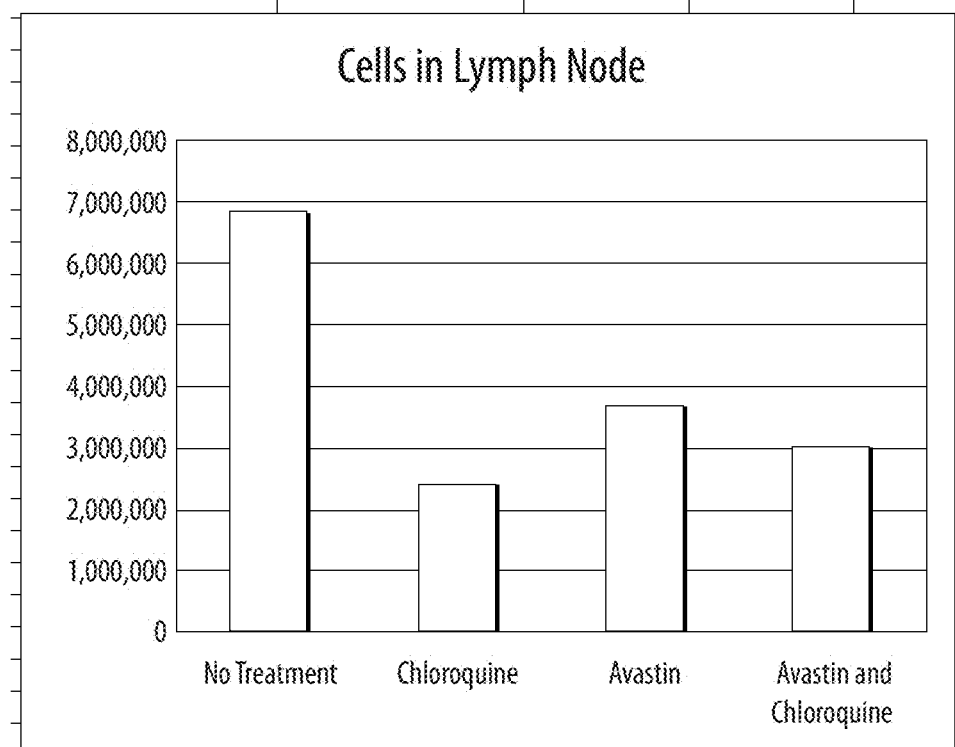
Figure 2B:
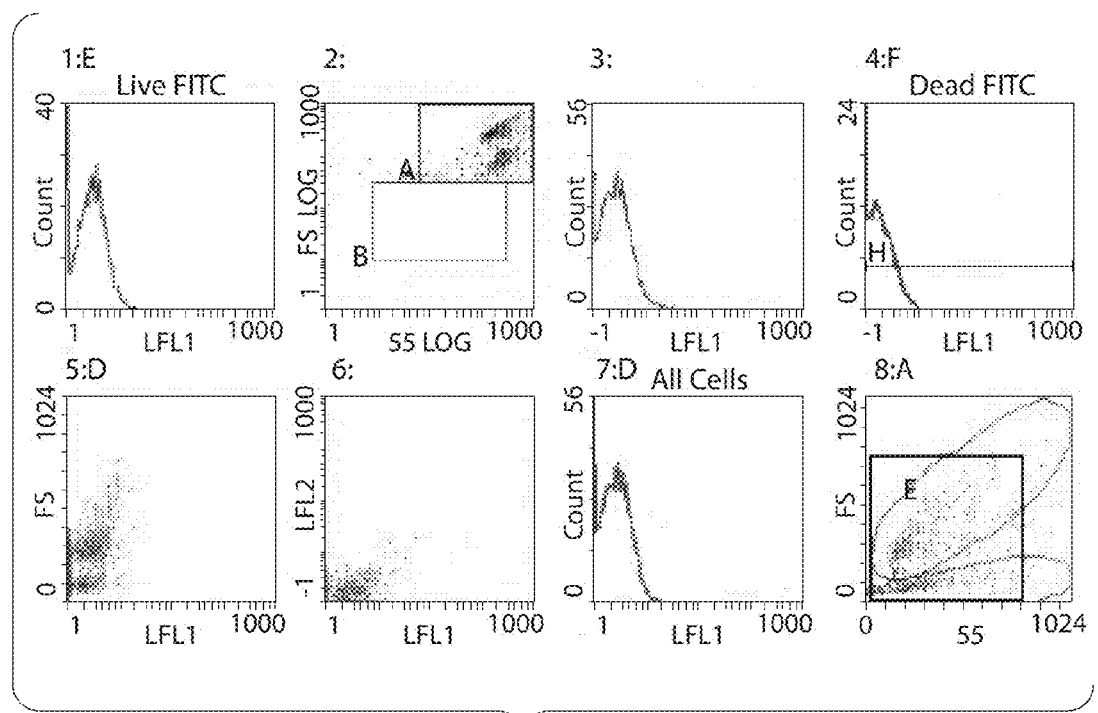
Figure 2C:
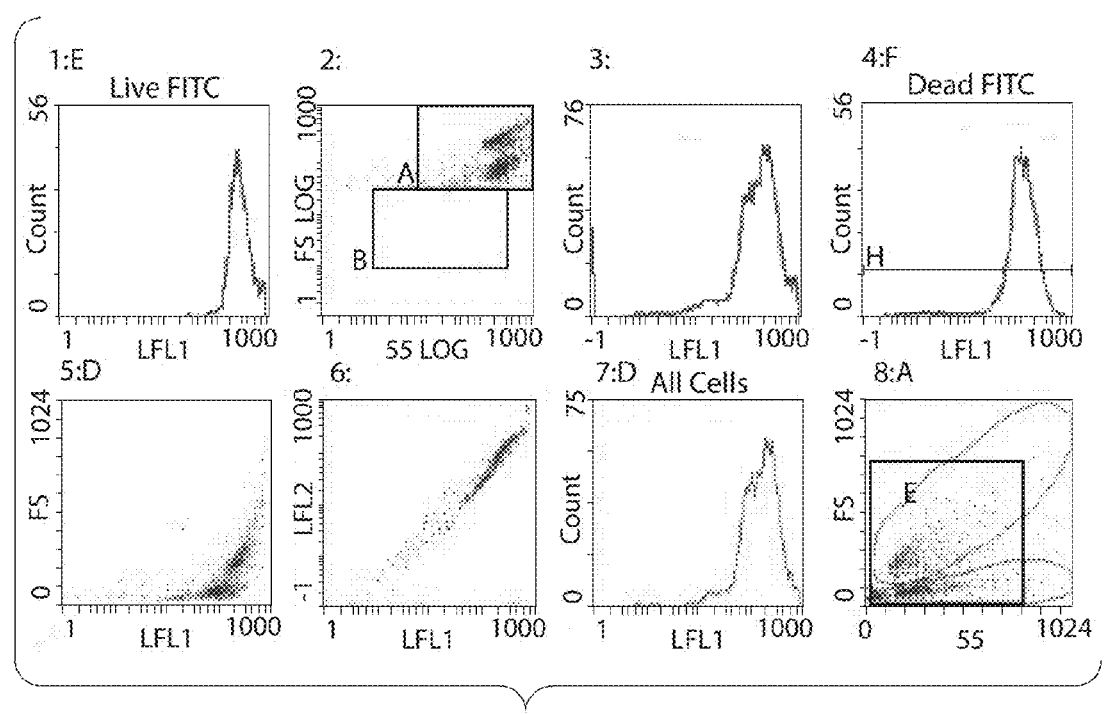
Figure 2D:
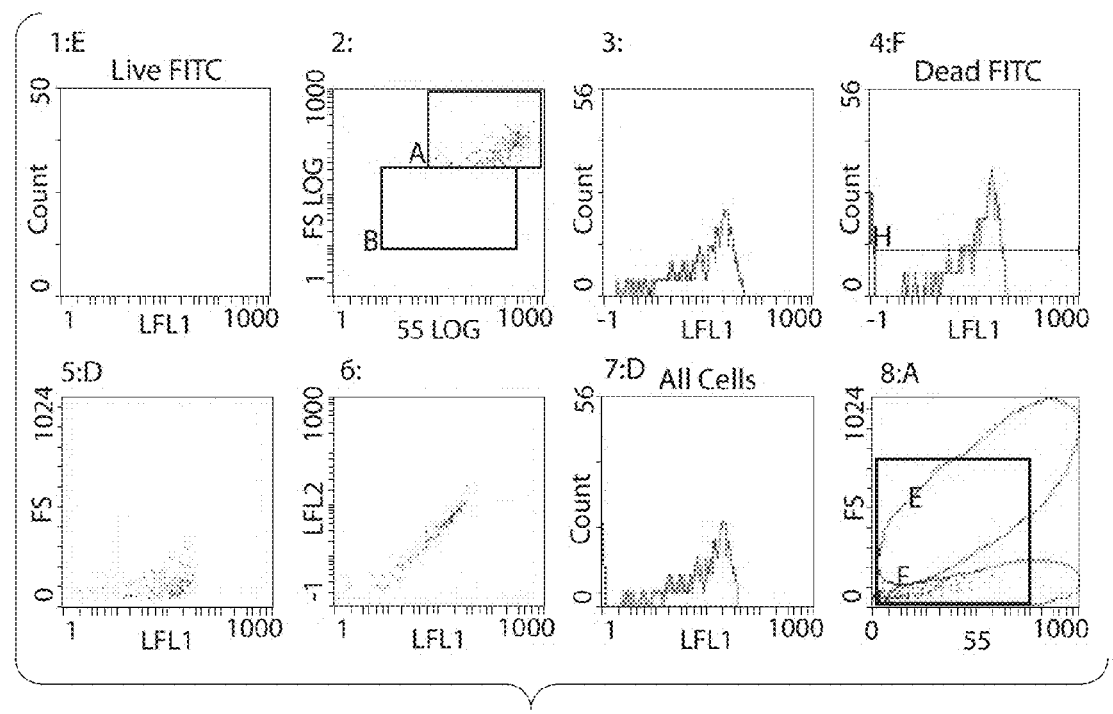
Figure 2E:
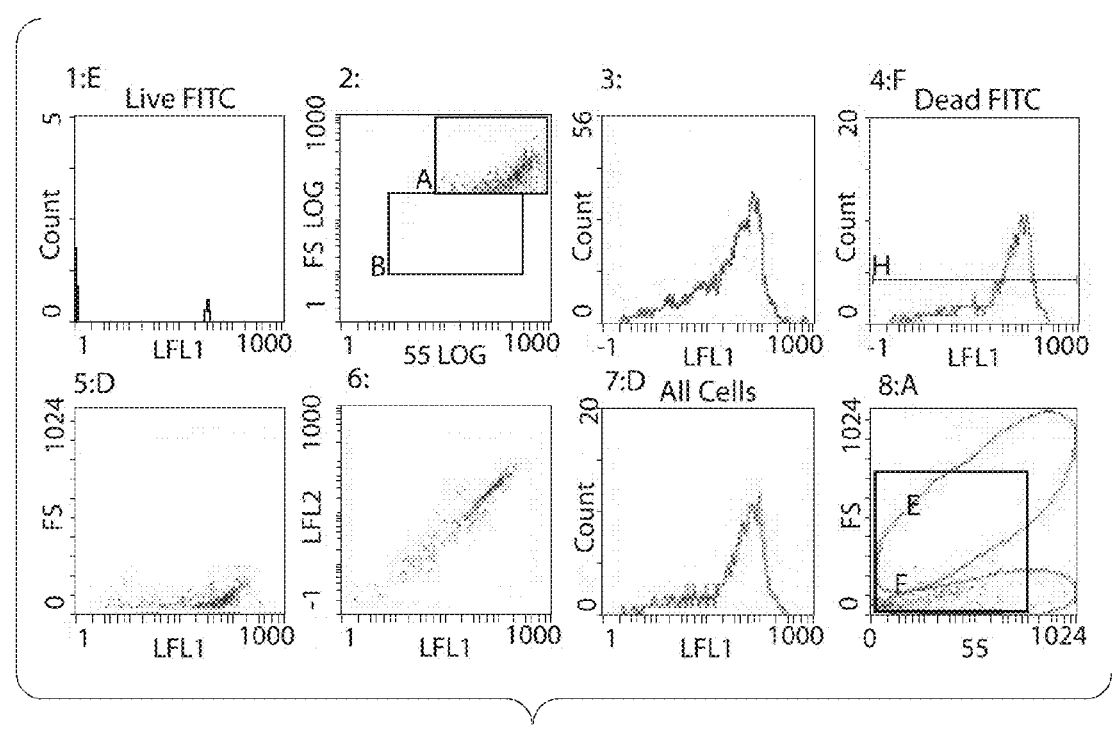
Figure 2F:
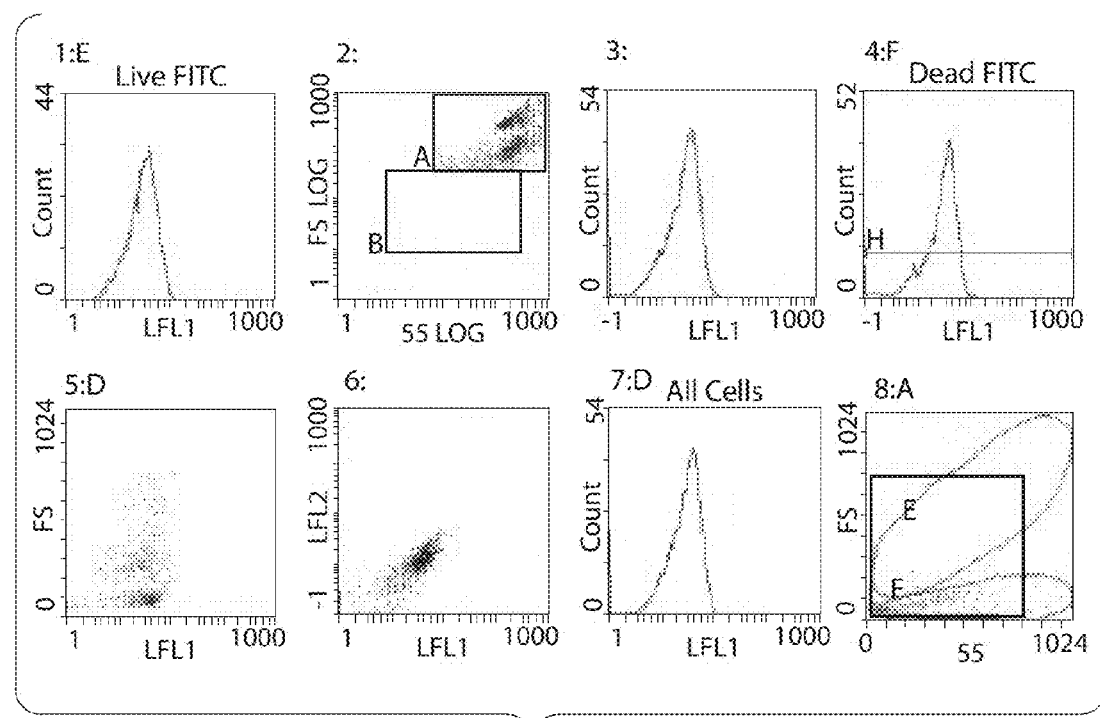
Figure 2G:
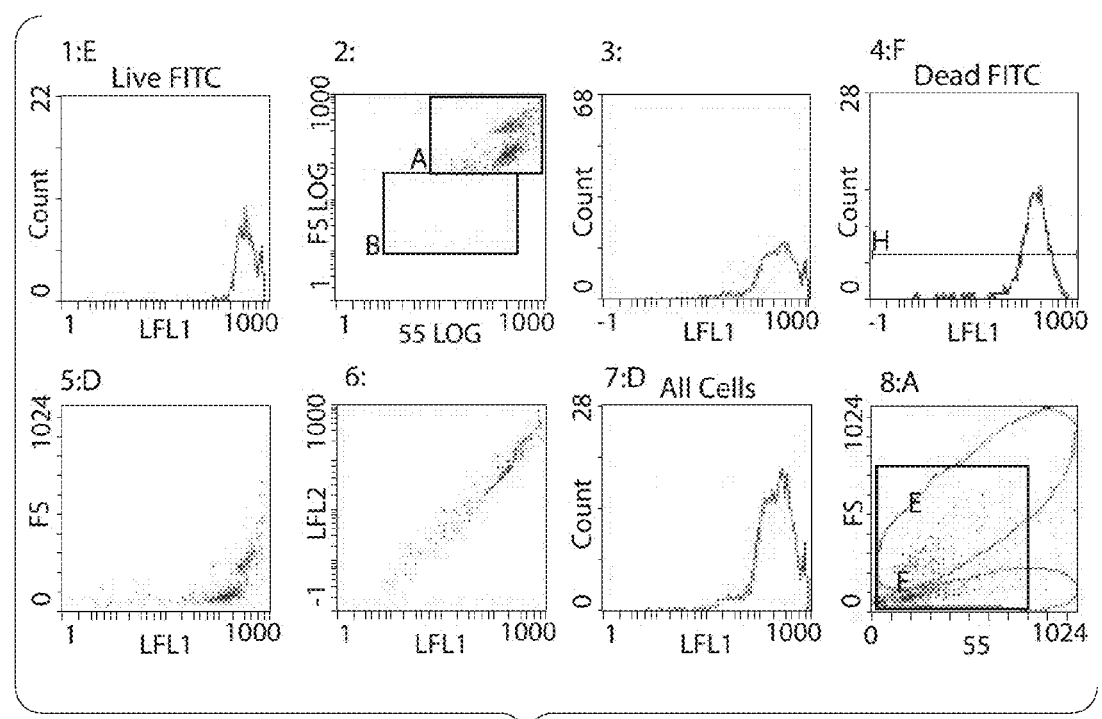
Figure 2H:
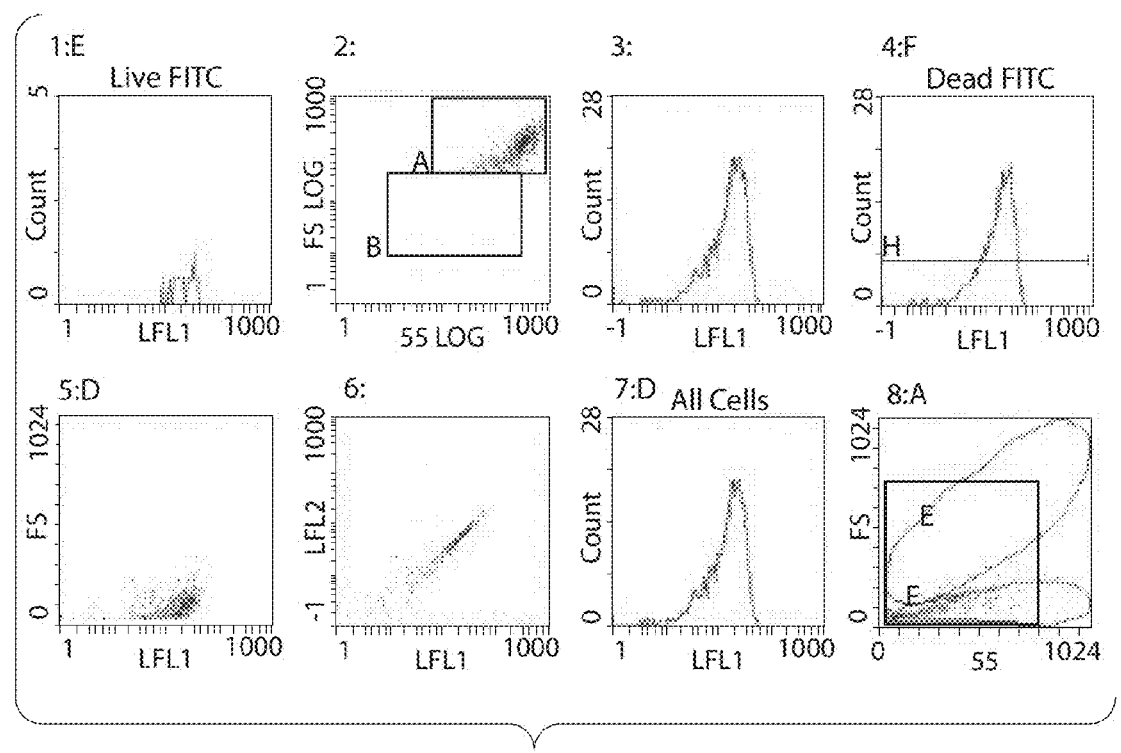
Figure 2I:
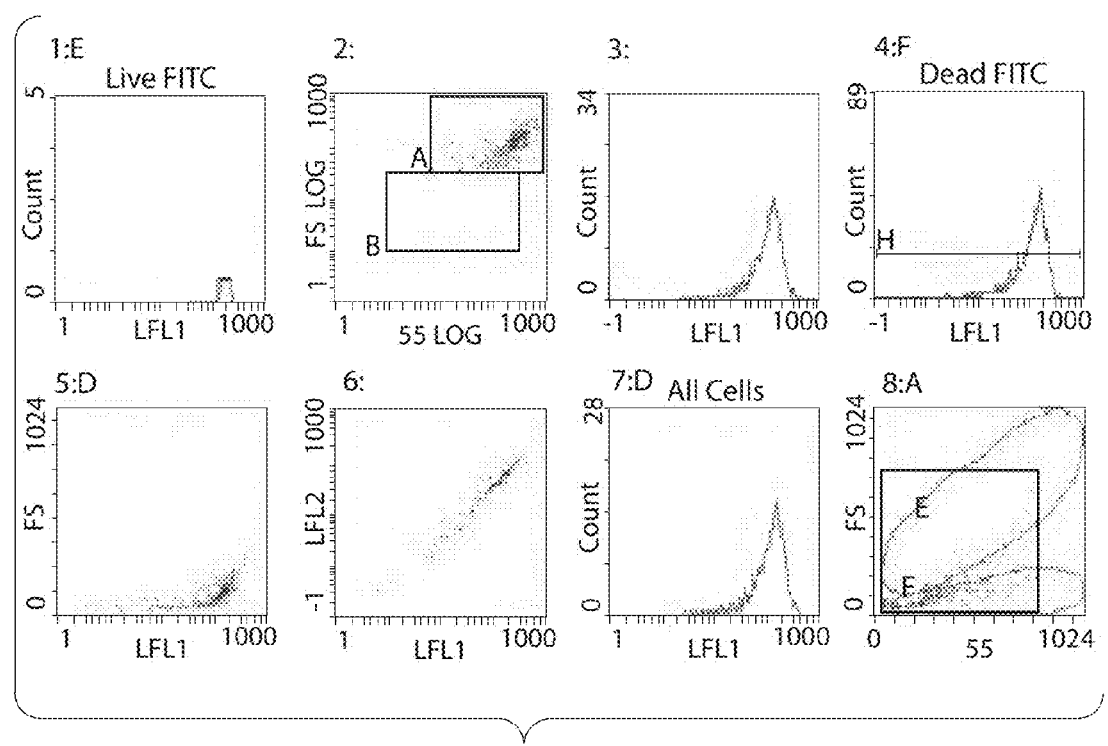
Figure 2J:
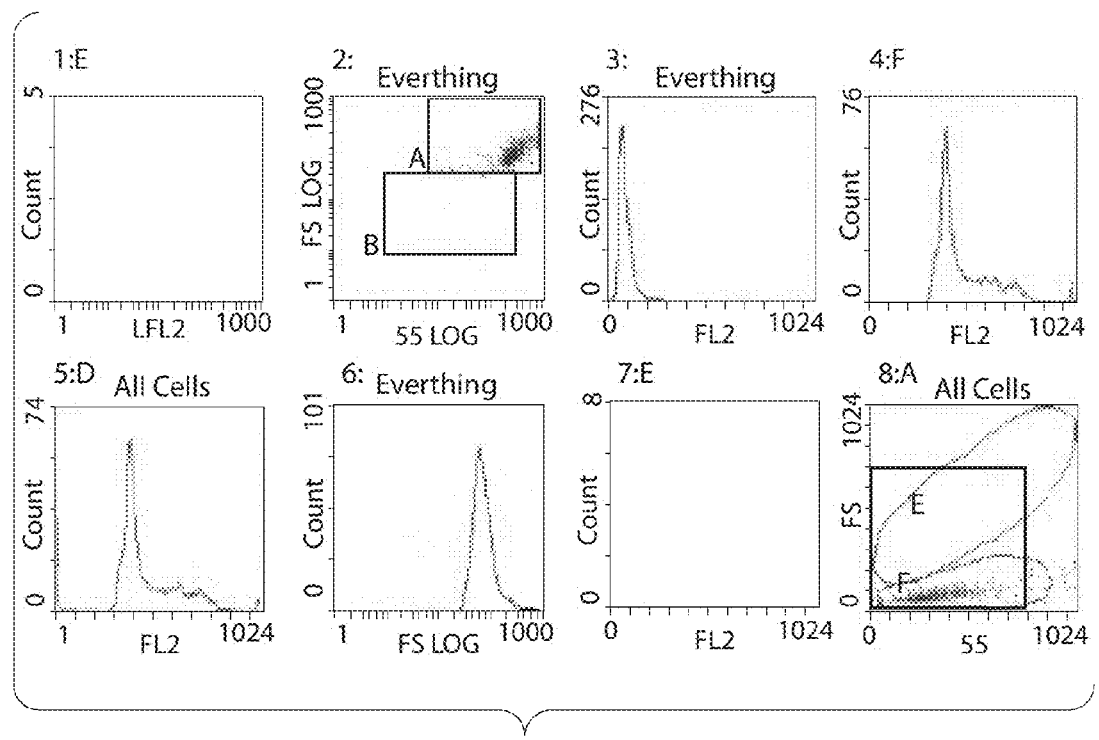
Figure 2K:
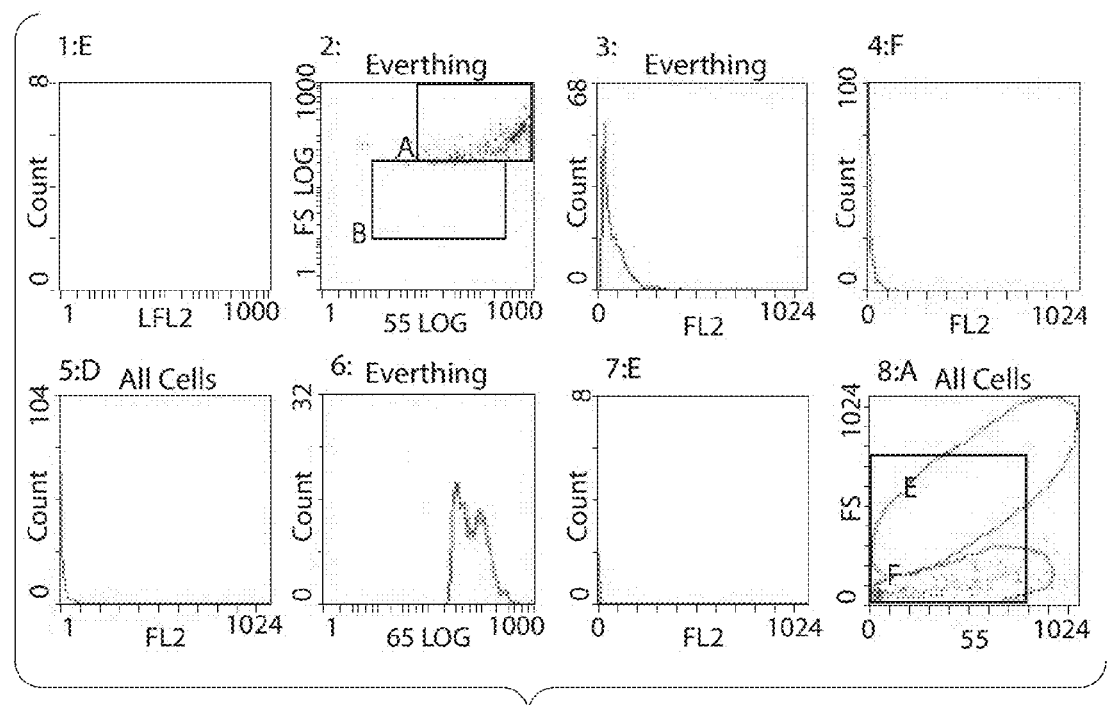
Figure 2L:
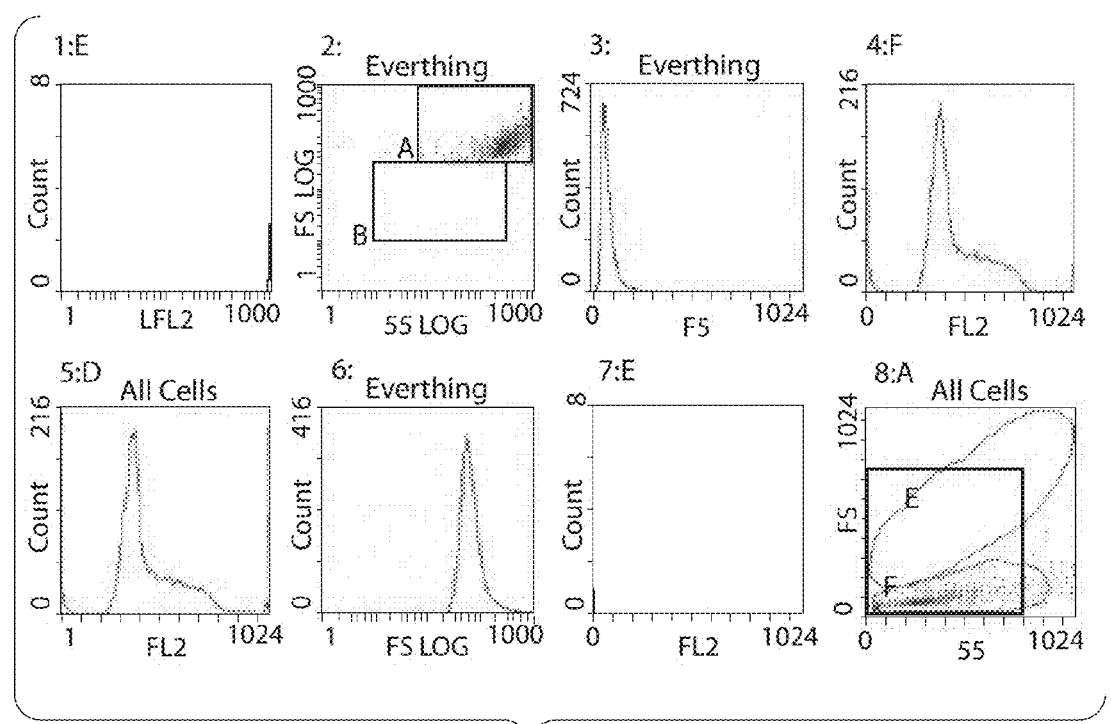
Figure 2M:
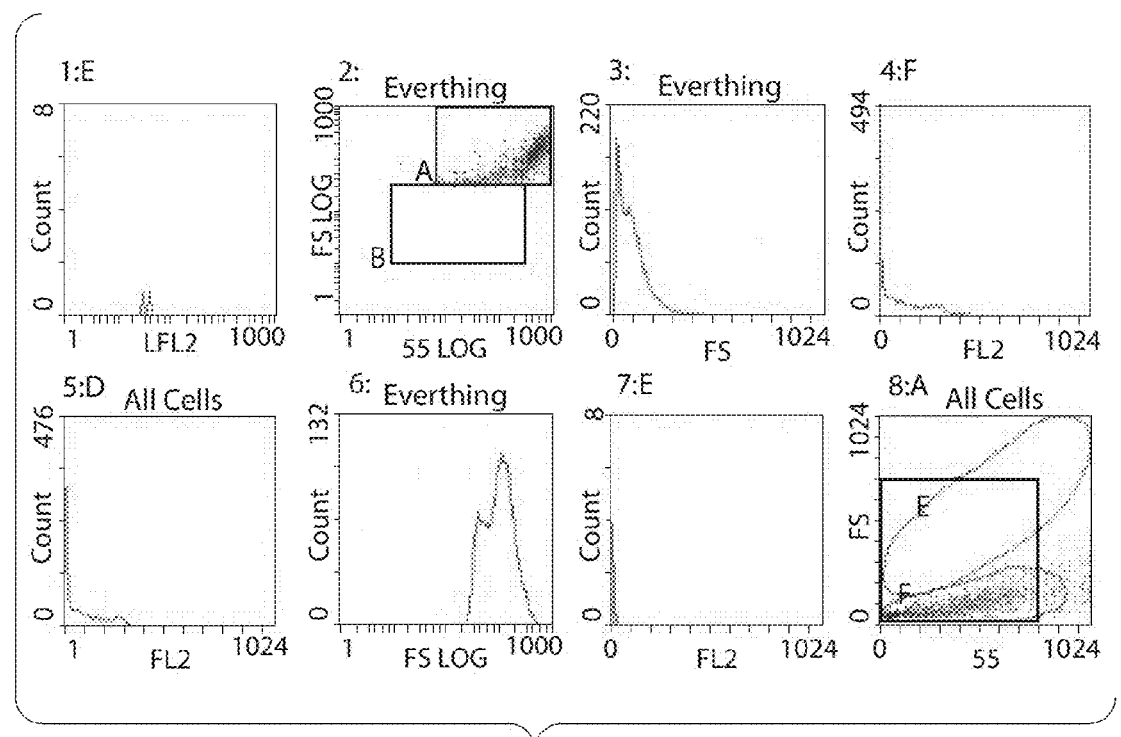

Other, non-limiting examples of fatty acid metabolism inhibitors include fatty acid transporter inhibitors, beta-oxidation process inhibitors, reductase inhibitors, and/or isomerase inhibitors within the fatty acid metabolism pathway. Specific examples of other fatty acid metabolism inhibitors include, but are not limited to, cerulenin, 5-(tetradecyloxy)-2-furoic acid, oxfenicine, methyl palmoxirate, metoprolol, amiodarone, perhexyline, aminocamitine, hydrazonopropionic acid, 4-bromocrotonic acid, trimetazidine, ranolazine, hypoglycin, dichloroacetate, methylene cyclopropyl acetic acid, and beta-hydroxy butyrate. Structural formulas for these inhibitors are shown in FIGS. 1A-1C. As a another example, the inhibitor may be a non-hydrolyzable analog of camitine.

In one embodiment, the fatty acid metabolism inhibitor is a carboxylic acid. In some cases, the carboxylic acid may have the structure:

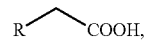

where R comprises an organic moiety, as further described below. In some cases, R may include at least two nitrogen atoms, or R may include an aromatic moiety (as further described below), such as a benzene ring, a furan, etc.

In another embodiment, the fatty acid metabolism inhibitor has the structure:

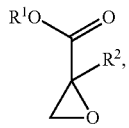

where each of $R^1$ and $R^2$ independently comprises organic moiety. In some instances, either or both of $R^1$ and $R^2$ may independently be an alkyl, such as a straight-chain alkyl, for instance, methyl, ethyl, propyl, etc. In certain cases, $R^2$ may have at least 5 carbon atoms, at least 10 carbon atoms, or at least 15 or more carbon atoms. For example, in one embodiment, $R^2$ may be a tetradecyl moiety. In other cases, $R^2$ may include an aromatic moiety, for example, a benzene ring. In still other cases, $R^2$ may have the structure:

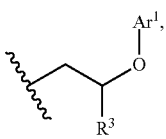

where $R^3$ comprises an organic moiety and $Ar^1$ comprises an aromatic moiety. $R^3$ may be a an alkyl, such as a straight-chain alkyl. In some instances, $Ar^1$ may be a benzene ring or a derivative thereof, i.e., having the structure:

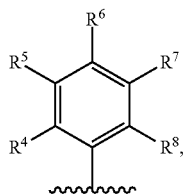

wherein each of $R^4$, $R^5$, $R^6$, $R^7$, and $R^8$ is hydrogen, a halogen, an alkyl, an alkoxy, etc.

In yet another embodiment, the fatty acid metabolism inhibitor has the structure:

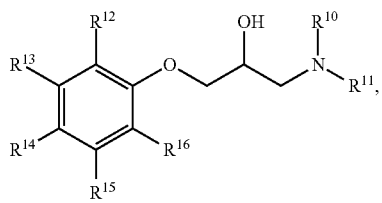

where each of $R^{10}$, $R^{11}$, $R^{12}$, $R^{13}$, $R^{14}$ $R^{15}$ and $R^{16}$ independently comprises hydrogen, a halogen, or an organic moiety, such as an alkyl, an alkoxy, etc. In some cases, $R^{10}$ and $R^{11}$ together may define an organic moiety, such as a cyclic group. For example, the fatty acid metabolism inhibitor may have the structure:

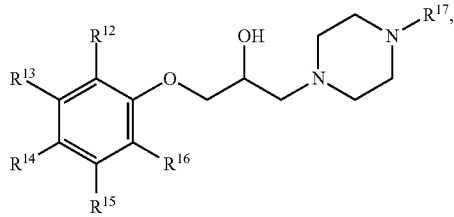

wherein $R^{17}$ comprises an organic moiety, such as an alkyl, an alkoxy, an aromatic moiety, an amide, etc. An example, of $R^{17}$ is:

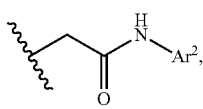

wherein $Ar^2$ comprises an aromatic moiety, such as a benzene ring or a benzene derivative, as previously described.

In still another embodiment, the fatty acid metabolism inhibitor includes a dominant negative plasma membrane polypeptide. The end result of the use (e.g., expression) of a dominant negative polypeptide in a cell may be a reduction in functional enzymes present within the fatty acid metabolism pathway. One of ordinary skill in the art can assess the potential for a dominant negative variant of a protein or enzyme, and use standard mutagenesis techniques to create one or more dominant negative variant polypeptides. For example, one of ordinary skill in the art can modify the sequence of an enzyme coding region by site-specific mutagenesis, scanning mutagenesis, partial gene deletion or truncation, and the like. See, e.g., U.S. Pat. No. 5,580,723 and Sambrook, et al., *Molecular Cloning: A Laboratory Manual*, Second Edition, Cold Spring Harbor Laboratory Press, 1989. One of ordinary skill in the art then can test the population of mutagenized polypeptides for diminution in a selected and/or for retention of such activity of the protein or enzyme. Other similar methods for creating and testing dominant negative variants of a protein will be apparent to one of ordinary skill in the art.

In another set of embodiments, the cells may be exposed to an agent that inhibits the synthesis or production of one or enzymes within the fatty acid metabolism pathway. Exposure of the cells to the agent thus inhibits fatty acid metabolism within the cell. For example, in one embodiment, an antisense oligonucleotide or siRNA may be used that selectively binds to regions encoding enzymes present within the fatty acid metabolism pathway, such as 2,4-dienoyl-CoA reductase or 2,4-dienoyl-CoA isomerase. Antisense and siRNA oligonucleotides are discussed in more detail below.

General Considerations

One or more other of the compounds described herein may be an isolated molecule in certain cases. An "isolated molecule," as used herein, is a molecule that is substantially pure and is free of other substances with which it is ordinarily found in nature or in vivo systems to an extent practical and appropriate for its intended use. In particular, the molecular species may be sufficiently pure and may be sufficiently free from other biological constituents of host cells so as to be useful in, for example, producing pharmaceutical preparations, or for sequencing, e.g., if the molecular species is a nucleic acid, peptide, or polysaccharide. Because an isolated molecular species of the invention may be admixed with a pharmaceutically-acceptable carrier in a pharmaceutical preparation, and/or other physiologically-active agents, the molecular species may comprise only a small percentage by weight of the preparation. The molecular species is nonetheless substantially pure in that it has been substantially separated from the substances with which it may be associated in living systems. As an example, an autophagy modulator may be associated with other molecules, such as a glucolytic inhibitor and/or a pharmaceutically acceptable carrier.

In some aspects of the invention, the systems and methods described herein have broad utility in regulating mammalian cell growth and death in vitro, in vivo, and/or ex vivo. For example, as further discussed below, the systems and methods of the invention may be used in the treatment of cancers, tumors, and other conditions involving rapidly dividing cell populations that may be uncontrolled.

The in vitro methods of the invention are useful for a variety of purposes. For instance, the systems and methods of the invention may be useful for identifying drugs which have an effect, such as a preventative effect, on cellular division, cancers, or cell death, by contacting cells manipulated by the invention to undergo cellular division or death upon exposure to putative compounds.

In addition to in vitro methods, certain methods of the invention may be performed in vivo or ex vivo in a subject to manipulate one or more other cell types within a subject. A "subject" as used herein, means a human or non-human mammal, including but not limited to, a dog, cat, horse, cow, pig, sheep, goat, chicken, primate, rat, and mouse. In vivo methods are well known in the art. Thus, the invention is useful for therapeutic purposes as well as research purposes, such as testing in animal or in vitro models of certain medical, physiological or metabolic pathways or conditions. An "ex vivo" method, as used herein, is a method which involves isolation of a cell from a subject, manipulation of the cell outside of the body, and reimplantation of the manipulated cell into the subject. The ex vivo procedure may be used on autologous or heterologous cells, and is typically used on autologous cells. In some embodiments, the ex vivo method is performed on cells that are isolated from bodily fluids, such as peripheral blood or bone marrow; however, the cells may be isolated from any source of cells. When returned to the subject, the manipulated cell can be programmed for cell death or division, depending on the treatment to which it was exposed. Ex vivo manipulation of cells has been described in several references in the art, including Engleman, *Cytotechnology*, 25:1, 1997; Van Schooten, et al., *Molecular Medicine Today*, June, 255, 1997; Steinman, *Experimental Hematology*, 24:849, 1996; and Gluckman, *Cytokines, Cellular and Molecular Therapy*, 3:187, 1997. The ex vivo activation of cells of the invention may be performed by routine ex vivo manipulation steps known in the art.

According to one aspect of the invention, the systems and methods described herein are useful in treating cancers, tumors, and other conditions involving rapidly dividing cell populations that are typically uncontrolled. A "rapidly dividing cell," as used herein, is a cell which is undergoing mitotic growth. Such cells are well known in the art and include, but are not limited to, tumor cells, cancer cells, lymphocytes (T cells or B cells), bacteria, and pancreatic beta ($\beta$) cells. Rapidly dividing cells, for example, cancer cells such as drug and multi-drug resistant cancer cells, are often able to derive a majority of their metabolic energy through fatty acid metabolism, i.e., the main source of energy (ATP) for the cancer cells comes from the oxidation of fatty acids instead of sugars such as glucose. Thus, in certain embodiments, the invention provides an inhibitor for a reaction of the fatty acid metabolism pathway, which, in some cases, may kill the rapidly dividing cells ("cytotoxic") or at least prevent the cells from further division and/or growth.

Thus, the systems and methods of the invention, in some embodiments, are useful for inducing cell death in many types of mammalian cells, for example, tumor cells. As used herein, the term "cell death" is used to refer to either of the processes of apoptosis or cell lysis. In both apoptosis and cell lysis, the cell dies, but the processes occur through different mechanisms and/or different metabolic states of the cell. Apoptosis is a process of cell death in which the cell undergoes shrinkage and fragmentation, followed by phagocytosis of the cell fragments. Apoptosis is well known in the art and can be assessed by any art-recognized method. For example, apoptosis can easily be determined using flow cytometry, which is able to distinguish between live and dead cells.

In one set of embodiments, the invention includes a method of treating a subject susceptible to or exhibiting symptoms of cancer. In some cases, the cancer is drug-resistant or multi-drug resistant. As used herein, a "drug-resistant cancer" is a cancer that is resistant to conventional commonly-known cancer therapies. Examples of conventional cancer therapies include treatment of the cancer with agents such as methotrexate, trimetrexate, adriamycin, taxotere, doxorubicin, 5-fluorouracil, vincristine, vinblastine, pamidronate disodium, anastrozole, exemestane, cyclophosphamide, epirubicin, toremifene, letrozole, trastuzumab, megestrol, tamoxifen, paclitaxel, docetaxel, capecitabine, goserelin acetate, etc. A "multi-drug resistant cancer" is a cancer that resists more than one type or class of cancer agents, i.e., the cancer is able to resist a first drug having a first mechanism of action, and a second drug having a second mechanism of action.

In some embodiments, the present invention provides a method of treating a cancer comprising administering to a subject in whom such treatment is desired a therapeutically effective amount of a composition cocktails of the invention. A composition of the invention may, for example, be used as a first, second, third or fourth line cancer treatment. In some embodiments, the invention provides methods for treating a cancer (including ameliorating a symptom thereof) in a subject refractory to one or more conventional therapies for such a cancer, said methods comprising administering to said subject a therapeutically effective amount of the compositions of the invention. A cancer may be determined to be refractory to a therapy when at least some significant portion of the cancer cells are not killed or their cell division are not arrested in response to the therapy. Such a determination can be made either in vivo or in vitro by any method known in the art for assaying the effectiveness of treatment on cancer cells, using the art-accepted meanings of "refractory" in such a context. In a specific embodiment, a cancer is refractory where the number of cancer cells has not been significantly reduced, or has increased.

Cancers that can be treated by the methods encompassed by the invention include, but are not limited to, neoplasms, malignant tumors, metastases, or any disease or disorder characterized by uncontrolled cell growth such that it would be considered cancerous. The cancer may be a primary or metastatic cancer. Specific cancers that can be treated according to the present invention include, but are not limited to, those listed below (for a review of such disorders, see Fishman et al., 1985, Medicine, 2d Ed., J.B. Lippincott Co., Philadelphia).

Cancers include, but are not limited to, biliary tract cancer; bladder cancer; brain cancer including glioblastomas and medulloblastomas; breast cancer; cervical cancer; choriocarcinoma; colon cancer; endometrial cancer; esophageal cancer; gastric cancer; hematological neoplasms including acute lymphocytic and myelogenous leukemia; multiple myeloma; AIDS-associated leukemias and adult T-cell leukemia lymphoma; intraepithelial neoplasms including Bowen's disease and Paget's disease; liver cancer; lung cancer; lymphomas including Hodgkin's disease and lymphocytic lymphomas; neuroblastomas; oral cancer including squamous cell carcinoma; ovarian cancer including those arising from epithelial cells, stromal cells, germ cells and mesenchymal cells; pancreatic cancer; prostate cancer; rectal cancer; sarcomas including leiomyosarcoma, rhabdomyosarcoma, liposarcoma, fibrosarcoma, and osteosarcoma; skin cancer including melanoma, Kaposi's sarcoma, basocellular cancer, and squamous cell cancer; testicular cancer including germinal tumors such as seminoma, non-seminoma, teratomas, choriocarcinomas; stromal tumors and germ cell tumors; thyroid cancer including thyroid adenocarcinoma and medullar carcinoma; and renal cancer including adenocarcinoma and Wilms' tumor. Commonly encountered cancers include breast, prostate, lung, ovarian, colorectal, and brain cancer. In some preferred embodiments of the invention, the compositions are used in the treatment of melanoma, ovarian cancer or glioblastoma.

The compositions of the invention also can be administered to prevent progression to a neoplastic or malignant state. Such prophylactic use is indicated in conditions known or suspected of preceding progression to neoplasia or cancer, in particular, where non-neoplastic cell growth consisting of hyperplasia, metaplasia, or most particularly, dysplasia has occurred (for review of such abnormal growth conditions, see Robbins and Angell, 1976, Basic Pathology, 2d Ed., W.B. Saunders Co., Philadelphia, pp. 68-79.). Hyperplasia is a form of controlled cell proliferation involving an increase in cell number in a tissue or organ, without significant alteration in structure or function. Endometrial hyperplasia often precedes endometrial cancer. Metaplasia is a form of controlled cell growth in which one type of adult or fully differentiated cell substitutes for another type of adult cell. Metaplasia can occur in epithelial or connective tissue cells. A typical metaplasia involves a somewhat disorderly metaplastic epithelium. Dysplasia is frequently a forerunner of cancer, and is found mainly in the epithelia; it is the most disorderly form of non-neoplastic cell growth, involving a loss in individual cell uniformity and in the architectural orientation of cells. Dysplastic cells often have abnormally large, deeply stained nuclei, and exhibit pleomorphism. Dysplasia characteristically occurs where there exists chronic irritation or inflammation, and is often found in the cervix, respiratory passages, oral cavity, and gall bladder.

Alternatively or in addition to the presence of abnormal cell growth characterized as hyperplasia, metaplasia, or dysplasia, the presence of one or more characteristics of a transformed phenotype, or of a malignant phenotype, displayed in vivo or displayed in vitro by a cell sample from a patient, can indicate the desirability of prophylactic/therapeutic administration of the composition of the invention. Such characteristics of a transformed phenotype include morphology changes, looser substratum attachment, loss of contact inhibition, loss of anchorage dependence, protease release, increased sugar transport, decreased serum requirement, expression of fetal antigens, disappearance of the 250,000 dalton cell surface protein, etc. (see also id., at pp. 84-90 for characteristics associated with a transformed or malignant phenotype).

In a specific embodiment, leukoplakia, a benign-appearing hyperplastic or dysplastic lesion of the epithelium, or Bowen's disease, a carcinoma in situ, are pre-neoplastic lesions indicative of the desirability of prophylactic intervention.

In another embodiment, fibrocystic disease (cystic hyperplasia, mammary dysplasia, particularly adenosis (benign epithelial hyperplasia)) is indicative of the desirability of prophylactic intervention. In one set of embodiments, the invention includes a method of treating a subject susceptible to or exhibiting symptoms of cancer. The cancer may be primary, metastatic, recurrent or multi-drug resistant, as mentioned above. In some cases, the cancer is drug-resistant or multi-drug resistant. As used herein, a "drug-resistant cancer" is a cancer that is resistant to conventional commonly-known cancer therapies. Examples of conventional cancer therapies include treatment of the cancer with agents such as methotrexate, trimetrexate, adriamycin, taxotere, doxorubic in, 5-fluorouracil, vincristine, vinblastine, pamidronate disodium, anastrozole, exemestane, cyclophosphamide, epirubicin, toremifene, letrozole, trastuzumab, megestrol, tamoxifen, paclitaxel, docetaxel, capecitabine, goserelin acetate, etc. A "multi-drug resistant cancer" is a cancer that resists more than one type or class of cancer agents, i.e., the cancer is able to resist a first drug having a first mechanism of action, and a second drug having a second mechanism of action.

In one embodiment, the methods of the invention can be used in conjunction with one or more other forms of cancer treatment, for example, in conjunction with an anti-cancer agent, chemotherapy, radiotherapy, etc. (e.g., simultaneously, or as part of an overall treatment procedure). The term "cancer treatment" as used herein, may include, but is not limited to, chemotherapy, radiotherapy, adjuvant therapy, vaccination, or any combination of these methods. Parameters of cancer treatment that may vary include, but are not limited to, dosages, timing of administration or duration or therapy; and the cancer treatment can vary in dosage, timing, or duration. Another treatment for cancer is surgery, which can be utilized either alone or in combination with any of the previously treatment methods. Any agent or therapy (e.g., chemotherapies, radiation therapies, surgery, hormonal therapies, and/or biological therapies/immunotherapies) which is known to be useful, or which has been used or is currently being used for the prevention or treatment of cancer can be used in combination with a composition of the invention in accordance with the invention described herein. One of ordinary skill in the medical arts can determine an appropriate treatment for a subject.

Examples of such agents (i.e., anti-cancer agents) include, but are not limited to, DNA-interactive agents including, but not limited to, the alkylating agents (e.g., nitrogen mustards, e.g. Chlorambucil, Cyclophosphamide, Isofamide, Mechlorethamine, Melphalan, Uracil mustard; Aziridine such as Thiotepa; methanesulphonate esters such as Busulfan; nitroso ureas, such as Carmustine, Lomustine, Streptozocin; platinum complexes, such as Cisplatin, Carboplatin; bioreductive alkylator, such as Mitomycin, and Procarbazine, Dacarbazine and Altretamine); the DNA strand-breakage agents, e.g., Bleomycin; the intercalating topoisomerase II inhibitors, e.g., Intercalators, such as Amsacrine, Dactinomycin, Daunorubicin, Doxorubicin, Idarubicin, Mitoxantrone, and nonintercalators, such as Etoposide and Teniposide; the nonintercalating topoisomerase II inhibitors, e.g., Etoposide and Teniposde; and the DNA minor groove binder, e.g., Plicamydin; the antimetabolites including, but not limited to, folate antagonists such as Methotrexate and trimetrexate; pyrimidine antagonists, such as Fluorouracil, Fluorodeoxyuridine, CB3717, Azacitidine and Floxuridine; purine antagonists such as Mercaptopurine, 6-Thioguanine, Pentostatin; sugar modified analogs such as Cytarabine and Fludarabine; and ribonucleotide reductase inhibitors such as hydroxyurea; tubulin Interactive agents including, but not limited to, colcbicine, Vincristine and Vinblastine, both alkaloids and Paclitaxel and cytoxan; hormonal agents including, but note limited to, estrogens, conjugated estrogens and Ethinyl Estradiol and Diethylstilbesterol, Chlortrianisen and Idenestrol; progestins such as Hydroxyprogesterone caproate, Medroxyprogesterone, and Megestrol; and androgens such as testosterone, testosterone propionate; fluoxymesterone, methyltestosterone; adrenal corticosteroid, e.g., Prednisone, Dexamethasone, Methylprednisolone, and Prednisolone; leutinizing hormone releasing hormone agents or gonadotropin-releasing hormone antagonists, e.g., leuprolide acetate and goserelin acetate; antihormonal antigens including, but not limited to, antiestrogenic agents such as Tamoxifen, antiandrogen agents such as Flutamide; and antiadrenal agents such as Mitotane and Aminoglutethimide; cytokines including, but not limited to, IL-1.alpha., IL-1 β, IL-2, IL-3, IL-4, IL-5, IL-6, IL-7, IL-8, IL-9, IL-10, IL-11, IL-12, IL-13, IL-18, TGF-β, GM-CSF, M-CSF, G-CSF, TNF-α, TNF-β, LAF, TCGF, BCGF, TRF, BAF, BDG, MP, LIF, OSM, TMF, PDGF, IFN-α, IFN-β, IFN-γ, and Uteroglobins (U.S. Pat. No. 5,696,092); anti-angiogenics including, but not limited to, agents that inhibit VEGF (e.g., other neutralizing antibodies (Kim et al., 1992; Presta et al., 1997; Sioussat et al., 1993; Kondo et al., 1993; Asano et al., 1995, U.S. Pat. No. 5,520,914), soluble receptor constructs (Kendall and Thomas, 1993; Aiello et al., 1995; Lin et al., 1998; Millauer et al., 1996), tyrosine kinase inhibitors (Siemeister et al., 1998, U.S. Pat. Nos. 5,639,757, and 5,792,771), antisense strategies, RNA aptamers and ribozymes against VEGF or VEGF receptors (Saleh et al., 1996; Cheng et al., 1996; Ke et al., 1998; Parry et al., 1999); variants of VEGF with antagonistic properties as described in WO 98/16551; compounds of other chemical classes, e.g., steroids such as the angiostatic 4,9(11)-steroids and C21-oxygenated steroids, as described in U.S. Pat. No. 5,972,922; thalidomide and related compounds, precursors, analogs, metabolites and hydrolysis products, as described in U.S. Pat. Nos. 5,712,291 and 5,593,990; Thrombospondin (TSP-1) and platelet factor 4 (PF4); interferons and metalloproteinase inhibitors; tissue inhibitors of metalloproteinases (TIMPs); anti-Invasive Factor, retinoic acids and paclitaxel (U.S. Pat. No. 5,716,981); AGM-1470 (Ingber et al., 1990); shark cartilage extract (U.S. Pat. No. 5,618,925); anionic polyamide or polyurea oligomers (U.S. Pat. No. 5,593,664); oxindole derivatives (U.S. Pat. No. 5,576,330); estradiol derivatives (U.S. Pat. No. 5,504,074); thiazolopyrimidine derivatives (U.S. Pat. No. 5,599,813); and LM609 (U.S. Pat. No. 5,753,230); apoptosis-inducing agents including, but not limited to, bcr-abl, bcl-2 (distinct from bell, cyclin D1; GenBank accession numbers M14745, X06487; U.S. Pat. Nos. 5,650,491; and 5,539,094) and family members including Bcl-x1, Mcl-1, Bak, A1, A20, and antisense nucleotide sequences (U.S. Pat. Nos. 5,650,491; 5,539,094; and 5,583,034); Immunotoxins and coaguligands, tumor vaccines, and antibodies.

Specific examples of anti-cancer agents which can be used in accordance with the methods of the invention include, but not limited to: acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflomithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; ilmofosine; interleukin II (including recombinant interieukin II, or rIL2), interferon alpha-2a; interferon alpha-2b; interferon alpha-n1; interferon alpha-n3; interferon beta-I a; interferon gamma-I b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; and zorubicin hydrochloride.

Other anti-cancer drugs include, but are not limited to: 20-epi-1,25 dihydroxyvitamin D3; 5-ethynyluracil; angiogenesis inhibitors; anti-dorsalizing morphogenetic protein-1; ara-CDP-DL-PTBA; BCR/ABL antagonists; CaRest M3; CARN 700; casein kinase inhibitors (ICOS); clotrimazole; collismycin A; collismycin B; combretastatin A4; crambescidin 816; cryptophycin 8; curacin A; dehydrodidemnin B; didemnin B; dihydro-5-azacytidine; dihydrotaxol, duocarmycin SA; kahalalide F; lamellarin-N triacetate; leuprolide+estrogen+progesterone; lissoclinamide 7; monophosphoryl lipid A+myobacterium cell wall sk; N-acetyldinaline; N-substituted benzamides; 06-benzylguanine; placetin A; placetin B; platinum complex; platinum compounds; platinum-triamine complex; rhenium Re 186 etidronate; RII retinamide; rubiginone B 1; SarCNU; sarcophytol A; sargramostim; senescence derived inhibitor 1; spicamycin D; tallimustine; 5-fluorouracil; thrombopoietin; thymotrinan; thyroid stimulating hormone; variolin B; thalidomide; velaresol; veramine;

verdins; verteporfin; vinorelbine; vinxaltine; vitaxin; zanoterone; zeniplatin; and zilascorb.

The invention also encompasses administration of the compositions of the invention in combination with radiation therapy comprising the use of x-rays, gamma rays and other sources of radiation to destroy the cancer cells. In preferred embodiments, the radiation treatment is administered as external beam radiation or teletherapy wherein the radiation is directed from a remote source. In other preferred embodiments, the radiation treatment is administered as internal therapy or brachytherapy wherein a radioactive source is placed inside the body close to cancer cells or a tumor mass.

In certain embodiments, the method for treating a subject involves administering to the subject in addition to the compounds described herein an effective amount of a nucleic acid such as a small interfering nucleic acid molecule such as antisense, RNAi, or siRNA oligonucleotide to reduce the level of VEGF expression or the level of expression of proteins involved in autophagy and the other metabolic pathways described herein. The nucleotide sequences of the proteins are all well known in the art and can be used by one of skill in the art using art recognized techniques in combination with the guidance set forth below to produce the appropriate siRNA molecules. Such methods are described in more detail below.

The invention features the use of small nucleic acid molecules, referred to as small interfering nucleic acid (siNA) that include, for example: microRNA (miRNA), small interfering RNA (siRNA), double-stranded RNA (dsRNA), and short hairpin RNA (shRNA) molecules. An siNA of the invention can be unmodified or chemically-modified. An siNA of the instant invention can be chemically synthesized, expressed from a vector or enzymatically synthesized as discussed herein. The instant invention also features various chemically-modified synthetic small interfering nucleic acid (siNA) molecules capable of modulating gene expression or activity in cells by RNA interference (RNAi). The use of chemically-modified siNA improves various properties of native siNA molecules through, for example, increased resistance to nuclease degradation in vivo and/or through improved cellular uptake. Furthermore, siNA having multiple chemical modifications may retain its RNAi activity. The siNA molecules of the instant invention provide useful reagents and methods for a variety of therapeutic applications.

Chemically synthesizing nucleic acid molecules with modifications (base, sugar and/or phosphate) that prevent their degradation by serum ribonucleases can increase their potency (see e.g., Eckstein et al., International Publication No. WO 92/07065; Perrault et al, 1990 Nature 344, 565; Pieken et al., 1991, Science 253, 314; Usman and Cedergren, 1992, Trends in Biochem. Sci. 17, 334; Usman et al., International Publication No. WO 93/15187; and Rossi et al., International Publication No. WO 91/03162; Sproat, U.S. Pat. No. 5,334,711; and Burgin et al., supra; all of these describe various chemical modifications that can be made to the base, phosphate and/or sugar moieties of the nucleic acid molecules herein). Modifications which enhance their efficacy in cells, and removal of bases from nucleic acid molecules to shorten oligonucleotide synthesis times and reduce chemical requirements are desired. (All these publications are hereby incorporated by reference herein).

There are several examples in the art describing sugar, base and phosphate modifications that can be introduced into nucleic acid molecules with significant enhancement in their nuclease stability and efficacy. For example, oligonucleotides are modified to enhance stability and/or enhance biological activity by modification with nuclease resistant groups, for example, 2' amino, 2'-C-allyl, 2'-fluoro, 2'-O-methyl, 2'-H, nucleotide base modifications (for a review see Usman and Cedergren, 1992, TIBS. 17, 34; Usman et al., 1994, Nucleic Acids Symp. Ser. 31, 163; Burgin et al., 1996, Biochemistry, 35, 14090). Sugar modification of nucleic acid molecules have been extensively described in the art (see Eckstein et al., International Publication PCT No. WO 92/07065; Perrault et al. Nature, 1990, 344, 565 568; Pieken et al. Science, 1991, 253, 314317; Usman and Cedergren, Trends in Biochem. Sci., 1992, 17, 334 339; Usman et al. International Publication PCT No. WO 93/15187; Sproat, U.S. Pat. No. 5,334,711 and Beigelman et al., 1995, J. Biol. Chem., 270, 25702; Beigelman et al., International PCT publication No. WO 97/26270; Beigelman et al., U.S. Pat. No. 5,716,824; Usman et al., molecule comprises one or more chemical modifications.

In one embodiment, one of the strands of the double-stranded siNA molecule comprises a nucleotide sequence that is complementary to a nucleotide sequence of a target RNA or a portion thereof, and the second strand of the double-stranded siNA molecule comprises a nucleotide sequence identical to the nucleotide sequence or a portion thereof of the targeted RNA. In another embodiment, one of the strands of the double-stranded siNA molecule comprises a nucleotide sequence that is substantially complementary to a nucleotide sequence of a target RNA or a portion thereof, and the second strand of the double-stranded siNA molecule comprises a nucleotide sequence substantially similar to the nucleotide sequence or a portion thereof of the target RNA. In another embodiment, each strand of the siNA molecule comprises about 19 to about 23 nucleotides, and each strand comprises at least about 19 nucleotides that are complementary to the nucleotides of the other strand.

In some embodiments an siNA is an shRNA, shRNA-mir, or microRNA molecule encoded by and expressed from a genomically integrated transgene or a plasmid-based expression vector. Thus, in some embodiments a molecule capable of inhibiting mRNA expression, or microRNA activity, is a transgene or plasmid-based expression vector that encodes a small-interfering nucleic acid. Such transgenes and expression vectors can employ either polymerase II or polymerase III promoters to drive expression of these shRNAs and result in functional siRNAs in cells. The former polymerase permits the use of classic protein expression strategies, including inducible and tissue-specific expression systems. In some embodiments, transgenes and expression vectors are controlled by tissue specific promoters. In other embodiments transgenes and expression vectors are controlled by inducible promoters, such as tetracycline inducible expression systems.

In some embodiments, a small interfering nucleic acid of the invention is expressed in mammalian cells using a mammalian expression vector. The recombinant mammalian expression vector may be capable of directing expression of the nucleic acid preferentially in a particular cell type (e.g., tissue-specific regulatory elements are used to express the nucleic acid). Tissue specific regulatory elements are known in the art. Non-limiting examples of suitable tissue-specific promoters include the myosin heavy chain promoter, albumin promoter, lymphoid-specific promoters, neuron specific promoters, pancreas specific promoters, and mammary gland specific promoters. Developmentally-regulated promoters are also encompassed, for example the murine hox promoters and the α-fetoprotein promoter.

Other inhibitor molecules that can be used include ribozymes, peptides, DNAzymes, peptide nucleic acids (PNAs), triple helix forming oligonucleotides, antibodies, and aptamers and modified form(s) thereof directed to sequences in gene(s), RNA transcripts, or proteins. Antisense and ribozyme suppression strategies have led to the reversal of a tumor phenotype by reducing expression of a gene product or by cleaving a mutant transcript at the site of the mutation (Carter and Lemoine Br. J. Cancer. 67(5):869-76, 1993; Lange et al., Leukemia. 6(11):1786-94, 1993; Valera et al., J. Biol. Chem. 269(46):28543-6, 1994; Dosaka-Akita et al., Am. J. Clin. Pathol. 102(5):660-4, 1994; Feng et al., Cancer Res. 55(10):2024-8, 1995; Quattrone et al., Cancer Res. 55(1):90-5, 1995; Lewin et al., Nat. Med. 4(8):967-71, 1998). For example, neoplastic reversion was obtained using a ribozyme targeted to an H-Ras mutation in bladder carcinoma cells (Feng et al., Cancer Res. 55(10):2024-8, 1995). Ribozymes have also been proposed as a means of both inhibiting gene expression of a mutant gene and of correcting the mutant by targeted trans-splicing (Sullenger and Cech Nature 371(6498):619-22, 1994; Jones et al., Nat. Med. 2(6): 643-8, 1996). Ribozyme activity may be augmented by the use of, for example, non-specific nucleic acid binding proteins or facilitator oligonucleotides (Herschlag et al., Embo J. 13(12):2913-24, 1994; Jankowsky and Schwenzer Nucleic Acids Res. 24(3):423-9, 1996). Multitarget ribozymes (connected or shotgun) have been suggested as a means of improving efficiency of ribozymes for gene suppression (Ohkawa et al., Nucleic Acids Symp Ser. (29):121-2, 1993).

Triple helix approaches have also been investigated for sequence-specific gene suppression. Triple helix forming oligonucleotides have been found in some cases to bind in a sequence-specific manner (Postel et al., Proc. Natl. Acad. Sci. U.S.A. 88(18):8227-31, 1991; Duval-Valentin et al., Proc. Natl. Acad. Sci. U.S.A. 89(2):504-8, 1992; Hardenbol and Van Dyke Proc. Natl. Acad. Sci. U.S.A. 93(7):2811-6, 1996; Porumb et al., Cancer Res. 56(3):515-22, 1996). Similarly, peptide nucleic acids have been shown to inhibit gene expression (Hanvey et al., Antisense Res. Dev. 1(4):307-17, 1991; Knudsen and Nielson Nucleic Acids Res. 24(3):494-500, 1996; Taylor et al., Arch. Surg. 132(11):1177-83, 1997). Minor-groove binding polyamides can bind in a sequence-specific manner to DNA targets and hence may represent useful small molecules for future suppression at the DNA level (Trauger et al., Chem. Biol. 3(5):369-77, 1996). In addition, suppression has been obtained by interference at the protein level using dominant negative mutant peptides and antibodies (Herskowitz Nature 329(6136):219-22, 1987; Rimsky et al., Nature 341(6241):453-6, 1989; Wright et al., Proc. Natl. Acad. Sci. U.S.A. 86(9):3199-203, 1989). In some cases suppression strategies have led to a reduction in RNA levels without a concomitant reduction in proteins, whereas in others, reductions in RNA have been mirrored by reductions in protein.

The diverse array of suppression strategies that can be employed includes the use of DNA and/or RNA aptamers that can be selected to target, for example VEGF. Suppression and replacement using aptamers for suppression in conjunction with a modified replacement gene and encoded protein that is refractory or partially refractory to aptamer-based suppression could be used in the invention.

In specific embodiments, an appropriate anti-cancer regimen is selected depending on the type of cancer. For instance, a patient with ovarian cancer may be administered a prophylactically or therapeutically effective amount of the compositions of the invention in combination with a prophylactically or therapeutically effective amount of one or more other agents useful for ovarian cancer therapy, including but not limited to, intraperitoneal radiation therapy, such as $P^{32}$ therapy, total abdominal and pelvic radiation therapy, cisplatin, the combination of paclitaxel (Taxol) or docetaxel (Taxotere) and cisplatin or carboplatin, the combination of cyclophosphamide and cisplatin, the combination of cyclophosphamide and carboplatin, the combination of 5-FU and leucovorin, etoposide, liposomal doxorubicin, gemcitabine or topotecan. In a particular embodiment, a prophylactically or therapeutically effective amount of a composition of the invention is administered in combination with the administration of Taxol for patients with platinum-refractory disease. A further embodiment is the treatment of patients with refractory cancer including administration of: ifosfamide in patients with disease that is platinum-refractory, hexamethylmelamine (HMM) as salvage chemotherapy after failure of cisplatin-based combination regimens, and tamoxifen in patients with detectable levels of cytoplasmic estrogen receptor on their tumors.

Cancer therapies and their dosages, routes of administration and recommended usage are known in the art and have been described in such literature as the *Physician's Desk Reference* ($56^{th}$ ed., 2002).

The invention, in still another set of embodiments, is useful for treating other diseases associated with rapidly dividing cells, such as rheumatoid arthritis and scleroderma. Rheumatoid arthritis is associated in its early stages with the rapid division of synoviocytes. This process is referred to a pannus formation. The rapidly dividing cells produce a substance that kills osteocytes leading to the hardening of the tissue.

In another aspect, the systems and methods of the invention are useful for treating or preventing disorders associated with a specific antigenic immune response. Thus, in some embodiments of the invention, the methods are used to treat mammals at risk of, or afflicted with, autoimmune disease. Autoimmune disease is a disorder in which the host's immune response is defective and results in the production of a specific immune response against the individual's own antigens or components. In an autoimmune disease, an individual's own antibodies react with host tissue or in which immune effector T cells are autoreactive to endogenous self peptides and cause destruction of tissue. It is well established that MI-IC class II alleles act as major genetic elements in susceptibility to a variety of autoimmune diseases. The structures recognized by T cells, the cells that cause autoimmunity, are complexes comprised of class II MHC molecules and antigenic peptides. When the T cells react with the host's class II MHC molecules-peptide complexes derived from a host's own gene products, autoimmune disease can result. If these class II MHC/peptide complexes are inhibited from being formed, the autoimmune response is reduced or suppressed, and thus is inhibited according to the invention. The peptide-antigen of autoimmune disorders are self-antigens. Any autoimmune disease in which class II MHC/peptide complexes play a role may be treated according to the methods of the present invention. Such autoimmune diseases include, but are not limited to, juvenile-onset diabetes (insulin-dependent), multiple sclerosis, pemphigus vulgaris, Graves disease, myasthenia gravis, systemic lupus erythematosus (SLE), celiac disease rheumatoid arthritis, and Hashimoto's thyroiditis. The invention includes a method for determining an individuals susceptibility to developing autoimmune disease. As used herein, "susceptibility to autoimmune disease" indicates a likelihood of at least greater than the average of developing autoimmune disease, and in some embodiments at least about 10% greater. Thus the invention also includes systems and methods for treating a subject having autoimmune disease to reduce associated cell death.

The methods of the invention also include methods for treating a subject having autoimmune disease to reduce associated cell death, according to one set of embodiments. One method is based on the ability to selectively remove gamma delta (γδ) T cells which specifically recognize MHC class II HLA-DR on the surface of a self cell. When the gamma delta T cells recognize a tissue having significant amounts of MHC class II HLA-DR these T cells become activated and proliferate in order to kill more of the recognized cells. The methods of treatment are based on the concept of eliminating the activated gamma delta T cells from the body. These cells can be removed by contacting a gamma delta T cell with an amount of a plasma membrane targeted UCP inhibitor in an amount effective to induce gamma delta T cell death. This selective killing of the gamma delta cells inhibits cell death associated with autoimmune disease.

In another aspect, the systems and methods of the invention are useful in treating wounds in subjects. As used herein, the term "wound" is used to describe skin wounds as well as tissue wounds. A "skin wound" is defined herein as a break in the continuity of skin tissue which is caused by direct injury to the skin. Skin wounds are generally characterized by several classes including punctures, incisions, including those produced by surgical procedures, excisions, lacerations, abrasions, atrophic skin, or necrotic wounds and burns. The systems and methods of the invention are useful for enhancing the healing of all wounds of the skin.

A "tissue wound," as used herein, is a wound to an internal organ, such as a blood vessel, intestine, colon, etc. The systems and methods of the invention are useful for enhancing the wound healing process in tissue wounds, whether they arise naturally, or as the result of surgery. For instance, during the repair of arteries an artery may need to be sealed and wound healing promoted as quickly as possible. The systems and methods of the invention can speed up that process in many cases. The invention may also be particularly useful for the treatment of damaged tissue in the colon. In addition to promoting wound healing of the damaged colon, in some cases, the systems and methods of the invention can provide an antimicrobial effect.

The cells treated according to the present invention may be used to treat a wound, for example cells exposed to an autophagy modulator and a glycolytic inhibitor. As an example, ex vivo cells may be attached to a bandage or other substrate, and the substrate positioned over a wound, at least partially covering the wound. In some cases, the bandage or other substrate may be adhered to the subject, for example, through the use of adhesives. Suitable adhesives can be selected by those of ordinary skill in the art; some suitable adhesives are further described below.

The systems and methods of the invention may also include additional therapeutic and/or pharmacologically acceptable agents. For instance, the compositions or methods may involve other agents for the treatment of wounds such as, for instance, dexpanthenol, growth factors, enzymes or hormones, povidon-iodide, fatty acids, such as cetylphridinium chloride, antibiotics, and analgesics. In some embodiments, the compositions may also include growth factors. Growth factors include, but are not limited to, fibroblast growth factor (FGF), FGF-1, FGF-2, FGF-4, platelet-derived growth factor (PDGF), insulin-binding growth factor (IGF), IGF-1, IGF-2, epidermal growth factor (EGF), transforming growth factor (TGF), TGF-alpha, TGF-beta, cartilage inducing factors-A and -B, osteoid-inducing factors, osteogenin and other bone growth factors, collagen growth factors, heparin-binding growth factor-1 or -2, and/or their biologically active derivatives. The compositions may also include antiseptics in some embodiments.

Optionally, in some embodiments, a targeting mechanism can be used to target one or more other compositions of the invention to a specific cell, tumor, wound, or the like. It is desirable in many instances to specifically target a cell type to increase the efficiency and specificity of administration of the composition, thus avoiding the effects that can damage or destroy unrelated cells. Thus, a delivery system which enables the delivery of such drugs specifically to target cells is provided. The delivery system may increase the efficacy of treatment and reduce the associated "side effects" of such treatment.

Methods of targeting drugs and other compositions to target cells (such as cancer cells or cells within a wound) are well known in the art. One method of targeting involves antibody or receptor targeting. Receptor or antibody targeting involves linking the compound of the invention to a ligand or an antibody which has an affinity for a receptor or cell surface molecule expressed on the desired target cell surface. Using this approach, a composition of the invention is intended to adhere to the target cell following formation of a ligand-receptor or antibody-cell surface antigen complex on the cell surface. The type of receptor or antibody used to target the cell will depend on the specific cell type being targeted. A target molecule may be attached by a peptide or other type of bond such as a sulfhydryl or disulfide bond. Targeting molecules are described, for instance in U.S. Pat. No. 5,849,718, as well as many other references.

In general, the targeting moiety can be coupled to a composition of the invention. The molecules may be directly coupled to one another, such as by conjugation, or may be indirectly coupled to one another where, for example, the targeting moiety is on the surface of a liposome and one or more other compositions of the invention are contained within the liposome. If the molecules are linked to one another, then the targeting moiety can be covalently or non-covalently bound to the compound of the invention in a manner that preserves the targeting specificity of the targeting moiety. As used herein, "linked" or "linkage" means two entities are bound to one another by any physiochemical means. It is important that the linkage be of such a nature that it does not impair substantially the effectiveness of the compositions of the invention or the binding specificity of the targeting moiety. Keeping these parameters in mind, any linkage known to those of ordinary skill in the art may be employed, covalent or noncovalent. Such means and methods of linkage are well known to those of ordinary skill in the art.

Linkages according to the invention need not be direct linkage. The compositions of the invention may be provided with functionalized groups to facilitate their linkage and/or linker groups may be interposed therebetween to facilitate their linkage. In some instances, the components of the present invention may be synthesized in a single process, whereby the composition is regarded as a single entity. For example, a targeting moiety specific for a tumor cell could be synthesized together with a VCP inhibitor and an autophagy modulator of the invention. These and other modifications are intended to be embraced by the present invention.

Specific examples of covalent bonds include those where bifunctional cross-linker molecules can be used. The cross-linker molecules may be homobifunctional or heterobifunctional, depending upon the nature of the molecules to be conjugated. Homobifunctional cross-linkers have two identical reactive groups. Heterobifunctional cross-linkers have two different reactive groups that allow sequential conjugation reaction. Various types of commercially available cross-linkers are reactive with one or more other of the following groups, such as primary amines, secondary amines, sulfhydriles, carboxyls, carbonyls and carbohydrates.

Non-covalent methods of conjugation also may be used to join the targeting moiety and the composition in some cases. Non-covalent conjugation may be accomplished by direct or indirect means, including hydrophobic interaction, ionic interaction, intercalation, binding to major or minor grooves of a nucleic acid, and other affinity interactions.

Covalent linkages may be noncleavable in physiological environments, or cleavable in physiological environments, such as linkers containing disulfide bonds. Such molecules may resist degradation and/or may be subject to different intracellular transport mechanisms. One of ordinary skill in the art will be able to ascertain, without undue experimentation, the preferred bond for linking the targeting moiety and the compositions of the invention, based on the chemical properties of the molecules being linked and the preferred characteristics of the bond, for a given application.

For indirect linkage, the targeting moiety may be part of a particle, such as a liposome, which is targeted to a specific cell type. The liposome, in turn, may contain the compositions of the invention. The manufacture of liposomes containing compositions of the invention is fully described in the literature. Many for example, are based upon cholesteric molecules as starting ingredients and/or phospholipids. They may be synthetically derived or isolated from natural membrane components. Virtually any hydrophobic substance can be used, including cholesteric molecules, phospholipids and fatty acids preferably of medium chain length (i.e., 12 to 20 carbons), for example, naturally occurring fatty acids of between 14 and 18 carbons in length. These molecules can be attached to one or more other compositions of the invention, for example, with the lipophilic anchor inserting into the membrane of a liposome and the compositions tethered on the surface of the liposome for targeting the liposome to the cell. In other cases, one or more other compositions of the invention may be present in the interior of the liposome.

Each of the compositions described herein (or portions thereof) may optionally be associated with a delivery system or vector, according to one aspect of the invention. In its broadest sense, a "vector" is any vehicle capable of facilitating: (1) delivery of a composition to a target cell or (2) uptake of a composition by a target cell, if uptake is important. Optionally, a "targeting ligand" (in addition to, or the same as, the plasma membrane targeting molecule) can be attached to the vector to selectively deliver the vector to a cell which expresses on its surface the cognate receptor for the targeting ligand. In this manner, the vector (containing one or more other compositions of the invention) can be selectively delivered to a cell in, e.g., a tumor, a wound, etc. In general, the vectors useful in the invention are divided into two classes: colloidal dispersion systems and biological vectors. Other example compositions that can be used to facilitate uptake by a target cell of compositions of the invention include calcium phosphate and other chemical mediators of intracellular transport, microinjection compositions, and electroporation.

Suitable vectors include plasmid vectors. Plasmid vectors have been extensively described in the art and are well-known to those of skill in the art. See e.g., Sambrook, et al., *Molecular Cloning: A Laboratory Manual*, Second Edition, Cold Spring Harbor Laboratory Press, 1989. Plasmid vectors have been found to be particularly advantageous for delivering genes to cells in vivo because of their inability to replicate within and integrate into a host genome. These plasmids, however, having a promoter compatible with the host cell, can express a peptide from a gene operatively encoded within the plasmid. Some commonly used plasmids include pBR322, pUC18, pUC19, pRC/CMV, SV40, and pBlueScript. Other plasmids are well-known to those of ordinary skill in the art. Additionally, plasmids may be custom designed using restriction enzymes and/or ligation reactions to remove and add specific fragments of DNA.

It has also been discovered that gene carrying plasmids can be delivered to the cells in vivo using bacteria. Modified forms of bacteria such as *Salmonella* can be transfected with the plasmid and can thus be used as delivery vehicles in some cases. The bacterial delivery vehicles can be administered to a host subject orally or by other administration means. The bacteria in some instances can pass through the gut barrier. High levels of expression have been established using this methodology.

Compaction agents also can be used alone, or in combination with, a vector of the invention. A "compaction agent," as used herein, refers to an agent, such as a histone, that neutralizes the negative charges on the nucleic acid and thereby permits compaction of the nucleic acid into a fine granule. Compaction of the nucleic acid facilitates the uptake of the nucleic acid by the target cell. The compaction agents can be used alone, i.e., to deliver the compositions in a form that is more efficiently taken up by the cell or, more preferably, in combination with one or more other of the above-described vectors.

In one aspect, the invention provides a method of administering any of the compositions described herein to a subject. When administered, the compositions are applied in a therapeutically effective, pharmaceutically acceptable amount as a pharmaceutically acceptable formulation. As used herein, the term "pharmaceutically acceptable" is given its ordinary meaning. Pharmaceutically acceptable compositions are generally compatible with other materials of the formulation and are not generally deleterious to the subject. Any of the compositions of the present invention may be administered to the subject in a therapeutically effective dose. The dose to the subject may be such that a therapeutically effective amount of one or more other active compounds reaches the active site(s) within the subject. A "therapeutically effective" or an "effective" dose, as used herein, means that amount necessary to delay the onset of, inhibit the progression of, halt altogether the onset or progression of, diagnose a particular condition being treated, or otherwise achieve a medically desirable result, i.e., that amount which is capable of at least partially preventing, reversing, reducing, decreasing, ameliorating, or otherwise suppressing the particular condition being treated. A therapeutically effective amount can be determined on an individual basis and will be based, at least in part, on consideration of the species of mammal, the mammal's age, sex, size, and health; the composition used, the type of delivery system used; the time of administration relative to the severity of the disease; and whether a single, multiple, or controlled-release dose regiment is employed. A therapeutically effective amount can be determined by one of ordinary skill in the art employing such factors and using no more than routine experimentation.

The terms "treat," "treated," "treating," and the like, when used herein, refer to administration of the systems and methods of the invention to a subject, which may, for example, increase the resistance of the subject to development or further development of cancers, to eliminate or at least control a cancer or a wound, and/or to reduce the severity of the cancer or wound. The pharmaceutical preparations of the invention are administered to subjects in effective amounts. When administered to a subject, effective amounts will depend on the particular condition being treated and the desired outcome. A therapeutically effective dose may be determined by those of ordinary skill in the art, for instance, employing factors such as those further described below and using no more than routine experimentation.

In administering the systems and methods of the invention to a subject, dosing amounts, dosing schedules, routes of administration, and the like may be selected so as to affect known activities of these systems and methods. Dosage may be adjusted appropriately to achieve desired drug levels, local or systemic, depending upon the mode of administration. The doses may be given in one or several administrations per day. As one example, if daily doses are required, daily doses may be from about 0.01 mg/kg/day to about 1000 mg/kg/day, and in some embodiments, from about 0.1 to about 100 mg/kg/day or from about 1 mg/kg/day to about 10 mg/kg/day. Parental administration, in some cases, may be from one to several orders of magnitude lower dose per day, as compared to oral doses. For example, the dosage of an active compound, when parentally administered, may be between about 0.1 micrograms/kg/day to about 10 mg/kg/day, and in some embodiments, from about 1 microgram/kg/day to about 1 mg/kg/day or from about 0.01 mg/kg/day to about 0.1 mg/kg/day. In some embodiments the dosage of chloroquine compound is 0.05 to 1 mg/kg per day, 0.2 to 0.6 mg/kg per day, up to about 10 mg/kg/day, more than about 0.1 mg/kg/day, more than about 1.0 mg/kg/day, less than about 50 mg/kg/day or less than about 10 mg/kg/day.

In some embodiments, the concentration of the active compound(s) of the composition, if administered systemically, is at a dose of about 1.0 mg to about 2000 mg for an adult of 70 kg body weight, per day. In other embodiments, the dose is about 10 mg to about 1000 mg/70 kg/day. In yet other embodiments, the dose is about 100 mg to about 500 mg/70 kg/day. If applied topically, the concentration may be about 0.1 mg to about 500 mg/g of ointment or other base, about 1.0 mg to about 100 mg/g of base, or about 30 mg to about 70 mg/g of base. The specific concentration partially depends upon the particular composition used, as some are more effective than others. The dosage concentration of the composition actually administered is dependent, at least in part, upon the particular disorder being treated, the final concentration of composition that is desired at the site of action, the method of administration, the efficacy of the particular composition, the longevity of the particular composition, and the timing of administration relative to the severity of the disease. Preferably, the dosage form is such that it does not substantially deleteriously effect the mammal.

The dosage may be given in some cases at the maximum amount while avoiding or minimizing any potentially detrimental side effects within the subject. The dosage actually administered can be dependent upon factors such as the final concentration desired at the active site, the method of administration to the subject, the efficacy of the composition, the longevity of the composition within the subject, the mode and/or timing of administration, the effect of concurrent treatments (e.g., as in a cocktail), etc. The dose delivered may also depend on conditions associated with the subject, and can vary from subject to subject in some cases. For example, the age, sex, weight, size, environment, physical conditions, active site of the cancer or wound, or current state of health of the subject may also influence the dose required and/or the concentration of the composition at the active site. Variations in dosing may occur between different individuals or even within the same individual on different days. These factors are well known to those of ordinary skill in the art and can be addressed with no more than routine experimentation. It is preferred that a maximum dose be used, that is, the highest safe dose according to sound medical judgment.

In the event that the response of a particular subject is insufficient at such doses, even higher doses (or effectively higher doses by a different, more localized delivery route) may be employed to the extent that subject tolerance permits. Multiple doses per day are also contemplated, in some cases, to achieve appropriate systemic levels within the subject or within the active site of the subject. In certain instances, dosing amounts, dosing schedules, routes of administration, and the like may be selected as described herein, whereby therapeutically effective levels of the composition are provided.

In certain embodiments where cancers are being treated, a composition of the invention is administered to a subject who has a family history of cancer, or to a subject who has a genetic predisposition for cancer. In other embodiments, the composition is administered to a subject who has reached a particular age, or to a subject more likely to get cancer. In yet other embodiments, the compositions is administered to subjects who exhibit symptoms of cancer (e.g., early or advanced). In still other embodiments, the composition may be administered to a subject as a preventive measure. In some embodiments, the inventive composition may be administered to a subject based on demographics or epidemiological studies, or to a subject in a particular field or career.

Administration of a composition of the invention to a subject may be accomplished by any medically acceptable method which allows the composition to reach its target. The particular mode selected will depend of course, upon factors such as those previously described, for example, the particular composition, the severity of the state of the subject being treated, the dosage required for therapeutic efficacy, etc. As used herein, a "medically acceptable" mode of treatment is a mode able to produce effective levels of the active compound(s) of the composition within the subject without causing clinically unacceptable adverse effects. The administration may be localized (i.e., to a particular region, physiological system, tissue, organ, or cell type) or systemic, depending on the condition being treated. For example, the composition may be administered orally, vaginally, rectally, buccally, pulmonary, topically, nasally, transdermally, through parenteral injection or implantation, via surgical administration, or any other method of administration where suitable access to a target is achieved. Examples of parenteral modalities that can be used with the invention include intravenous, intradermal, subcutaneous, intracavity, intramuscular, intraperitoneal, epidural, or intrathecal. Examples of implantation modalities include any implantable or injectable drug delivery system. Oral administration may be preferred in some embodiments because of the convenience to the subject as well as the dosing schedule. Compositions suitable for oral administration may be presented as discrete units such as hard or soft capsules, pills, cachettes, tablets, troches, or lozenges, each containing a predetermined amount of the composition. Other oral compositions suitable for use with the invention include solutions or suspensions in aqueous or non-aqueous liquids such as a syrup, an elixir, or an emulsion. In one set of embodiments, the composition may be used to fortify a food or a beverage.

Injections can be e.g., intravenous, intradermal, subcutaneous, intramuscular, or interperitoneal. For example, the inhibitor can be injected intravenously or intramuscularly for the treatment of multiple sclerosis, or can be injected directly into the joints for treatment of arthritic disease, or can be injected directly into the lesions for treatment of pemphigus vulgaris. The composition can be injected interdermally for treatment or prevention of infectious disease, for example. In some embodiments, the injections can be given at multiple locations. Implantation includes inserting implantable drug delivery systems, e.g., microspheres, hydrogels, polymeric reservoirs, cholesterol matrixes, polymeric systems, e.g., matrix erosion and/or diffusion systems and non-polymeric systems, e.g., compressed, fused, or partially-fused pellets. For systemic administration, it may be useful to encapsulate the composition in liposomes.

Inhalation includes administering the composition with an aerosol in an inhaler, either alone or attached to a carrier that can be absorbed.

In general, the compositions of the invention may be delivered using a bioerodible implant by way of diffusion, or more preferably, by degradation of the polymeric matrix. Exemplary synthetic polymers which can be used to form the biodegradable delivery system include: polyamides, polycarbonates, polyalkylenes, polyalkylene glycols, polyalkylene oxides, polyalkylene terepthalates, polyvinyl alcohols, polyvinyl ethers, polyvinyl esters, poly-vinyl halides, polyvinylpyrrolidone, polyglycolides, polysiloxanes, polyurethanes and copolymers thereof, alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulphate sodium salt, poly(methyl methacrylate), poly(ethyl methacrylate), poly(butylmethacrylate), poly(isobutyl methacrylate), poly(hexylmethacrylate), poly (isodecyl methacrylate), poly(lauryl methacrylate), poly (phenyl methacrylate), poly(methyl acrylate), poly(isopropyl acrylate), poly(isobutyl acrylate), poly(octadecyl acrylate), polyethylene, polypropylene, poly(ethylene glycol), poly (ethylene oxide), poly(ethylene terephthalate), poly(vinyl alcohols), polyvinyl acetate, poly vinyl chloride, polystyrene, polyvinylpyrrolidone, and polymers of lactic acid and glycolic acid, polyanhydrides, poly(ortho)esters, poly(butic acid), poly(valeric acid), and poly(lactide-co-caprolactone), and natural polymers such as alginate and other polysaccharides including dextran and cellulose, collagen, chemical derivatives thereof (substitutions, additions of chemical groups, for example, alkyl, alkylene, hydroxylations, oxidations, and other modifications routinely made by those of ordinary skill in the art), albumin and other hydrophilic proteins, zein and other prolamines and hydrophobic proteins, copolymers and mixtures thereof. In general, these materials degrade either by enzymatic hydrolysis or exposure to water in vivo, by surface or bulk erosion. Examples of non-biodegradable polymers include ethylene vinyl acetate, poly(meth) acrylic acid, polyamides, copolymers and mixtures thereof.

Bioadhesive polymers of particular interest in some cases include, but are not limited to, the bioerodible hydrogels described by Sawhney, et al., *Macromolecules*, 26:581-587, 1993, the teachings of which are incorporated herein, as well as polyhyaluronic acids, casein, gelatin, glutin, polyanhydrides, polyacrylic acid, alginate, chitosan, poly(methyl methacrylates), poly(ethyl methacrylates), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate).

The systems and methods of the invention can be administered by any method which allows the composition of the invention to reach the target cells, e.g., tumor cells. These methods include, e.g., injection, infusion, deposition, implantation, anal or vaginal supposition, oral ingestion, inhalation, topical administration, or any other method of administration where access to the target cells by the inhibitor is obtained. In some embodiments, topical administration is preferred, due to the high concentration of APCs in the skin. One method for accomplishing topical administration includes transdermal administration, such as iontophoresis. Iontophoretic transmission can be accomplished by using commercially-available patches which deliver a compound continuously through unbroken skin for periods of hours to days to weeks, depending on the particular patch. This method allows for the controlled delivery of the composition through the skin in relatively high concentrations. One example of an iontophoretic patch is the LECTRO PATCH™ sold by General Medical Company of Los Angeles, Calif. The patch provides dosages of different concentrations which can be continuously or periodically administered across the skin using electronic stimulation of reservoirs containing the composition. Topical administration also includes epidermal administration which involves the mechanical or chemical irritation of the outermost layer of the epidermis sufficiently to provoke an immune response to the irritant. The irritant attracts APCs to the site of irritation where they can then take up the composition. One example of a mechanical irritant is a tyne-containing device. Such a device contains tynes which irritate the skin and deliver the drug at the same time, for instance, the MONO VACC™ manufactured by Pasteur Merieux of Lyon, France. The device contains a syringe plunger at one end and a tyne disk at the other. The tyne disk supports several narrow diameter tynes which are capable of scratching the outermost layer of epidermal cells. Chemical irritants include, for instance, keratinolytic agents, such as salicylic acid, and can be used alone or in conjunction with other irritants such as mechanical irritants.

In certain embodiments of the invention, the administration of the composition of the invention may be designed so as to result in sequential exposures to the composition over a certain time period, for example, hours, days, weeks, months, or years. This may be accomplished, for example, by repeated administration of a composition of the invention by one of the methods described above, and/or by a sustained or controlled release delivery system in which the composition is delivered over a prolonged period, usually without repeated administrations. Administration of the composition using such a delivery system may be, for example, by oral dosage forms, bolus injections, transdermal patches or subcutaneous implants. Maintaining a substantially constant concentration of the composition may be desirable in some cases.

Other delivery systems suitable for use with the present invention include time-release, delayed release, sustained release, or controlled release delivery systems. Such systems may avoid repeated administrations in many cases, increasing convenience to the subject and the physician. Many types of release delivery systems are available and known to those of ordinary skill in the art. They include, for example, polymer-based systems such as polylactic and/or polyglycolic acids, polyanhydrides, polycaprolactones, copolyoxalates, polyesteramides, polyorthoesters, polyhydroxybutyric acid, and/or combinations of these. Microcapsules of the foregoing polymers containing drugs are described in, for example, U.S. Pat. No. 5,075,109. Other examples include nonpolymer systems that are lipid-based including sterols such as cholesterol, cholesterol esters, and fatty acids or neutral fats such as mono-, di- and triglycerides, hydrogel release systems, liposome-based systems, phospholipid based-systems, silastic systems, peptide based systems, wax coatings, compressed tablets using conventional binders and excipients, or partially fused implants. Specific examples include, but are not limited to, erosional systems in which the composition is contained in a form within a matrix (for example, as described in U.S. Pat. Nos. 4,452,775, 4,675,189, 5,736,152, 4,667,014, 4,748,034 and 5,239,660), or diffusional systems in which an active component controls the release rate (for example, as described in U.S. Pat. Nos. 3,832,253, 3,854,480, 5,133,974 and 5,407,686). The formulation may be present as, for example, microspheres, hydrogels, polymeric reservoirs, cholesterol matrices, or polymeric systems. In some embodiments, the system may allow sustained or controlled release of the composition to occur, for example, through control of the diffusion or erosion/degradation rate of the formulation containing the composition. In addition, a pump-based hardware delivery system may be used to deliver one or more other embodiments of the invention in some cases.

Examples of systems in which release occurs in bursts includes, e.g., systems in which the composition is entrapped in liposomes which are encapsulated in a polymer matrix, the liposomes being sensitive to specific stimuli, e.g., temperature, pH, light or a degrading enzyme and systems in which the composition is encapsulated by an ionically-coated microcapsule with a microcapsule core-degrading enzyme. Examples of systems in which release of the inhibitor is gradual and continuous include, e.g., erosional systems in which the composition is contained in a form within a matrix and effusional systems in which the composition permeates at a controlled rate, e.g., through a polymer. Such sustained release systems can be e.g., in the form of pellets, or capsules.

Use of a long-term release implant may be particularly suitable in some embodiments of the invention. "Long-term release," as used herein, means that the implant containing the composition is constructed and arranged to deliver therapeutically effective levels of the composition for at least 30 or 45 days, and preferably at least 60 or 90 days, or even longer in some cases. Long-term release implants are well known to those of ordinary skill in the art, and include some of the release systems described above.

In certain embodiments of the invention, a composition may include a suitable pharmaceutically acceptable carrier, for example, as incorporated into a liposome, incorporated into a polymer release system, or suspended in a liquid, e.g., in a dissolved form or a colloidal form, such as in a colloidal dispersion system. In general, pharmaceutically acceptable carriers suitable for use in the invention are wellknown to those of ordinary skill in the art. As used herein, a "pharmaceutically acceptable carrier" refers to a non-toxic material that does not significantly interfere with the effectiveness of the biological activity of the active compound(s) to be administered, but is used as a formulation ingredient, for example, to stabilize or protect the active compound(s) within the composition before use. The term "carrier" denotes an organic or inorganic ingredient, which may be natural or synthetic, with which one or more other active compounds of the invention are combined to facilitate the application of the composition. The carrier may be co-mingled or otherwise mixed with one or more other active compounds of the present invention, and with each other, in a manner such that there is no interaction which would substantially impair the desired pharmaceutical efficacy. The carrier may be either soluble or insoluble, depending on the application. Examples of well-known carriers include glass, polystyrene, polypropylene, polyethylene, dextran, nylon, amylase, natural and modified cellulose, polyacrylamide, agarose and magnetite. The nature of the carrier can be either soluble or insoluble. Those skilled in the art will know of other suitable carriers, or will be able to ascertain such, using only routine experimentation.

As used herein, a "colloidal dispersion system" refers to a natural or synthetic molecule, other than those derived from bacteriological or viral sources, capable of delivering to and releasing the composition in a subject. Colloidal dispersion systems include macromolecular complexes, nanocapsules, microspheres, beads, and lipid-based systems including oil-in-water emulsions, micelles, mixed micelles, and liposomes. A preferred colloidal system of the invention is a liposome. Liposomes are artificial membrane vessels which are useful as a delivery vector in vivo or in vitro. It has been shown that large unilamellar vessels (LUV), which range in size from 0.2 micrometers to 4.0 micrometers can encapsulate large macromolecules within the aqueous interior and these macromolecules can be delivered to cells in a biologically active form (Fraley, et al., *Trends Biochem. Sci.*, 6:77, 1981).

Lipid formulations for transfection are commercially available, e.g., from QIAGEN, for example as EFFECTENE™ (a non-liposomal lipid with a special DNA condensing enhancer) and SUPER-FECT™ (a novel acting dendrimeric technology) as well as Gibco BRL, for example, as LIPOFECTIN™ and LIPOFECTACE™, which are formed of cationic lipids such as N-[1-(2,3-dioleyloxy)-propyl]-N,N, N-trimethylammonium chloride (DOTMA) and dimethyl dioctadecylammonium bromide (DDAB). Methods for making liposomes are well known in the art and have been described in many publications. Some liposomes were described in a review article by Gregoriadis, *Trends in Biotechnol.*, 3:235-241, 1985, which is hereby incorporated by reference.

In one embodiment, the vehicle is a biocompatible microparticle or implant that is suitable for implantation into the mammalian recipient. Exemplary bioerodible implants that are useful in accordance with this method are described in PCT International Application No. PCT/US/03307 (Publication No. WO 95/24929, entitled "Polymeric Gene Delivery System." PCT/US/0307 describes a biocompatible, preferably biodegradable polymeric matrix for containing an exogenous gene under the control of an appropriate promoter. The polymeric matrix is used to achieve sustained release of the exogenous gene in the subject. In accordance with the present invention, the compositions of the invention described herein can be encapsulated or dispersed within the biocompatible, optionally biodegradable polymeric matrix disclosed in PCT/US/03307.

The polymeric matrix can be in the form of a microparticle such as a microsphere (where the composition is dispersed throughout a solid polymeric matrix) or a microcapsule (where the composition is stored in the core of a polymeric shell). Other forms of the polymeric matrix for containing the composition include films, coatings, gels, implants, and stents. The size and composition of the polymeric matrix device can be selected to result in favorable release kinetics in the tissue into which the matrix is introduced. The size of the polymeric matrix can also be selected according to the method of delivery which is to be used, typically injection into a tissue or administration of a suspension by aerosol into the nasal and/or pulmonary areas. When an aerosol route is used the polymeric matrix and composition can be encompassed in a surfactant vehicle. The polymeric matrix composition can be selected to have both favorable degradation rates and/or to be formed of a material which is bioadhesive, e.g., to further increase the effectiveness of transfer when the matrix is administered to a nasal and/or pulmonary surface that has sustained an injury. The matrix composition can also be selected not to degrade, but rather, to release by diffusion over an extended period of time. In another embodiment, the matrix is a biocompatible microsphere that is suitable for oral delivery. Such microspheres are disclosed in Chickering, et al., *Biotech. and Bioeng.,* 52:96-101, 1996, and Mathiowitz, et al., *Nature,* 386:410-414, 1997.

Both non-biodegradable and biodegradable polymeric matrices can be used to deliver the compositions of the invention to the subject. Such polymers may be natural or synthetic polymers. The polymer may be selected based on the period of time over which release is desired, generally in the order of a few hours, to a year or longer. Typically, release over a period ranging from between a few hours and three to twelve months is desirable. The polymer optionally is in the form of a hydrogel that can absorb up to about 90% of its weight in water and further, optionally is cross-linked with multivalent ions or other polymers.

In some embodiments, the compositions of the invention may include pharmaceutically acceptable carriers with formulation ingredients such as salts, carriers, buffering agents, emulsifiers, diluents, excipients, chelating agents, fillers, drying agents, antioxidants, antimicrobials, preservatives, binding agents, bulking agents, silicas, solubilizers, or stabilizers. For example, if the formulation is a liquid, the carrier may be a solvent, partial solvent, or non-solvent, and may be aqueous or organically based. Examples of suitable formulation ingredients include diluents such as calcium carbonate, sodium carbonate, lactose, kaolin, calcium phosphate, or sodium phosphate; granulating and disintegrating agents such as corn starch or algenic acid; binding agents such as starch, gelatin or acacia; lubricating agents such as magnesium stearate, stearic acid, or talc; time-delay materials such as glycerol monostearate or glycerol distearate; suspending agents such as sodium carboxymethylcellulose, methylcellulose, hydroxypropylmethylcellulose, sodium alginate, polyvinylpyrrolidone; dispersing or wetting agents such as lecithin or other naturally-occurring phosphatides; thickening agents such as cetyl alcohol or beeswax; buffering agents such as acetic acid and salts thereof, citric acid and salts thereof, boric acid and salts thereof, or phosphoric acid and salts thereof; or preservatives such as benzalkonium chloride, chlorobutanol, parabens, or thimerosal. Suitable carrier concentrations can be determined by those of ordinary skill in the art, using no more than routine experimentation. The compositions of the invention may be formulated into preparations in solid, semi-solid, liquid or gaseous forms such as tablets, capsules, elixirs, powders, granules, ointments, solutions, depositories, inhalants or injectables. Those of ordinary skill in the art will know of other suitable formulation ingredients, or will be able to ascertain such, using only routine experimentation.

Preparations include sterile aqueous or nonaqueous solutions, suspensions and emulsions, which can be isotonic with the blood of the subject in certain embodiments. Examples of nonaqueous solvents are polypropylene glycol, polyethylene glycol, vegetable oil such as olive oil, sesame oil, coconut oil, arachis oil, peanut oil, mineral oil, injectable organic esters such as ethyl oleate, or fixed oils including synthetic mono or di-glycerides. Aqueous carriers include water, alcoholic/aqueous solutions, emulsions or suspensions, including saline and buffered media. Parenteral vehicles include sodium chloride solution, 1,3-butandiol, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents and inert gases and the like. In addition, sterile, fixed oils are conventionally employed as a solvent or suspending medium. For this purpose, any bland fixed oil may be employed including synthetic mono- or di-glycerides. In addition, fatty acids such as oleic acid may be used in the preparation of injectables. Carrier formulation suitable for oral, subcutaneous, intravenous, intramuscular, etc. administrations can be found in, for example, *Remington's Pharmaceutical Sciences*, Mack Publishing Co. Those of ordinary skill in the art can readily determine the various parameters for preparing and formulating the compositions of the invention without resort to undue experimentation.

In some embodiments, the present invention includes the step of forming a composition of the invention by bringing an active compound into association or contact with a suitable carrier, which may constitute one or more other accessory ingredients. The final composition may be prepared by any suitable technique, for example, by uniformly and intimately bringing the composition into association with a liquid carrier, a finely divided solid carrier or both, optionally with one or more other formulation ingredients as previously described, and then, if necessary, shaping the product.

In some embodiments, the compositions of the present invention may be present as pharmaceutically acceptable salts. The term "pharmaceutically acceptable salts" includes salts of the composition, prepared in combination with, for example, acids or bases, depending on the particular compounds found within the composition and the treatment modality desired. Pharmaceutically acceptable salts can be prepared as alkaline metal salts, such as lithium, sodium, or potassium salts; or as alkaline earth salts, such as beryllium, magnesium or calcium salts. Examples of suitable bases that may be used to form salts include ammonium, or mineral bases such as sodium hydroxide, lithium hydroxide, potassium hydroxide, calcium hydroxide, magnesium hydroxide, and the like. Examples of suitable acids that may be used to form salts include inorganic or mineral acids such as hydrochloric, hydrobromic, hydroiodic, hydrofluoric, nitric, carbonic, monohydrogencarbonic, phosphoric, monohydrogenphosphoric, dihydrogenphosphoric, sulfuric, monohydrogensulfuric, phosphorous acids and the like. Other suitable acids include organic acids, for example, acetic, propionic, isobutyric, maleic, malonic, benzoic, succinic, suberic, fumaric, mandelic, phthalic, benzenesulfonic, p-tolylsulfonic, citric, tartaric, methanesulfonic, glucuronic, galacturonic, salicylic, formic, naphthalene-2-sulfonic, and the like. Still other suitable acids include amino acids such as arginate, aspartate, glutamate, and the like.

In one aspect, the present invention provides any of the above-mentioned compositions in kits, optionally including instructions for use of the composition e.g., for the treatment of cancers or wounds. The "kit" typically defines a package including one or more other compositions of the invention and the instructions, or homologs, analogs, derivatives, enantiomers and functionally equivalent compositions thereof. That is, the kit can include a description of use of the composition for participation in any biological or chemical mechanism disclosed herein associated with cancers or wounds. The kits can further include a description of activity of the cancers or wounds in treating the pathology, as opposed to the symptoms. The kit can include a description of use of the compositions as discussed herein. The kit also can include instructions for use of a combination of two or more compositions of the invention, or instruction for use of a combination of a composition of the invention and one or more other other compounds indicated for treatment of a cancer, a wound, etc. Instructions also may be provided for administering the composition by any suitable technique as previously described, for example, orally, intravenously, pump or implantable delivery device, or via another known route of drug delivery. The instructions may be of any form provided in connection with the composition in a manner such that a clinical professional will clearly recognize that the instructions are to be associated with the specific composition.

The kits described herein may also contain one or more other containers, which may contain the inventive composition and other ingredients as previously described. The kits also may contain instructions for mixing, diluting, and/or administrating the compositions in some cases. The kits also can include other containers with one or more other solvents, surfactants, preservative and/or diluents (e.g., normal saline (0.9% NaCl), or 5% dextrose) as well as containers for mixing, diluting or administering the components to a subject in need of such treatment.

The compositions of the kit may be provided as any suitable form, for example, as liquid solutions or as dried powders. When the composition provided is a dry powder, the composition may be reconstituted by the addition of a suitable solvent, which may also be provided. In embodiments where liquid forms of the composition are used, the liquid form may be concentrated or ready to use. The solvent will depend on the active compound(s) within the composition and the mode of use or administration. Suitable solvents are well known, for example as previously described, and are available in the literature. The solvent will depend on the compound and the mode of use or administration.

The invention also involves, in another aspect, promotion of the treatment of cancers, wounds, etc. according to any of the systems or methods described herein. In some embodiments, one or more other compositions of the invention may be promoted for treatment of cancers or wounds, or include instructions for treatment of cancers or wounds. In some cases, the invention provides a method involving promoting the prevention or treatment of cancers, wounds, etc. via administration of any one of the compositions of the present invention, and homologs, analogs, derivatives, enantiomers and functionally equivalent compositions thereof in which the invention is able to treat cancer, wounds, etc. As used herein, "promoted" includes all methods of doing business including methods of education, hospital and other clinical instruction, pharmaceutical industry activity including pharmaceutical sales, and any advertising or other promotional activity including written, oral and electronic communication of any form, associated with compositions of the invention in connection with treatment of cancers or wounds. "Instructions" can define a component of promotion, and typically involve written instructions on or associated with packaging of compositions of the invention. Instructions also can include any oral or electronic instructions provided in any manner.

EXAMPLES

The following examples illustrate the invention with the use of an autophagy inhibitor and a glycolytic inhibitor, bevacizumab, alone or in combination with a chemotherapeutic, to induce tumor cell death.

Example 1

Methods
Tumor cells (B16.F1, NIT-1, or MCF7) were thawed from liquid nitrogen. The tumor cells were transferred into a 15 milliliter (ml) conical tube using a sterile bulb pipette. Using a balance, the tubes were balanced with cells and spun in the centrifuge. The liquid was removed using the vacuum, leaving the pellet of cells. The cells were mixed using two mls of the RPMI. In a 24 well plate, 1 ml of RPMI was placed in each well. One ml of cells was placed into the first well and the second ml was missed into the second well, then one ml was transferred from the second well into the third. The process was repeated until one ml will remain for the last well (serial dilutions). After two to three days the cells were confluent enough to transfer from a well into a flask. After around 24 hours the treatments were added to the appropriate flasks (control, chloroquine, Avastin, both). After 48 hrs. the cells were stained using lysotracker and propidium iodide. The plate was run in the flow cytometer to check the growth arrest and the amount of lysosomic activity as well as the amount of cell death.

B16.F1 cells were injected into mice. intra-dermally using a tuberculin syringe with a 27-gage needle. Each injection site receives approximately 750,000 B16F1 cells (that are suspended in 200 microliters of PBS) into each of their sides.

After the tumors were visible, four mice were treated and one mouse received no treatment. The first mouse received chloroquine, the second mouse received Avastin™ (antibody to VEGF), the third mouse received both chloroquine and Avastin™, the fourth mouse was the control.

Results
Referring to FIGS. 1 through 4, data are provided showing in vitro and in vivo results. In vivo, the photographs in FIG. 1 shows animals that have been injected with approximately 1 million tumor cells for 10 days. After one week, the animals were treated daily as indicated on the photographs with no treatment, daily injections of chloroquine using 20 microliters of 0.5 M chloroquine, using 10 microliters of 1 microgram/microliter avastin, or both as indicated. The tumors were measured daily. When the animals were sacrificed, the numbers of cells in the lymph nodes were counted and analyzed flow cytometrically.

Figure 3:
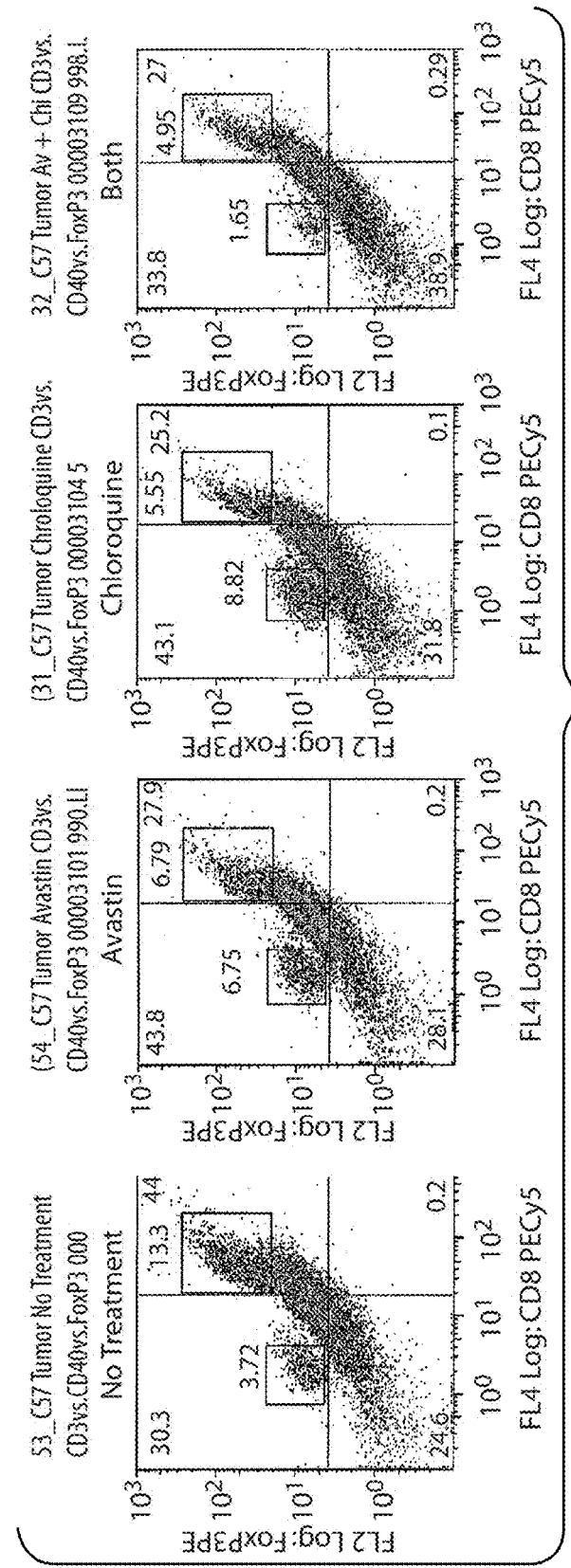
FIG. 3 shows the percent death in vitro using treatment with chloroquine, treatment with bevacizumab (Avastin®), and treatment with bevacizumab plus chloroquine, in cell culture.
Figure 4:
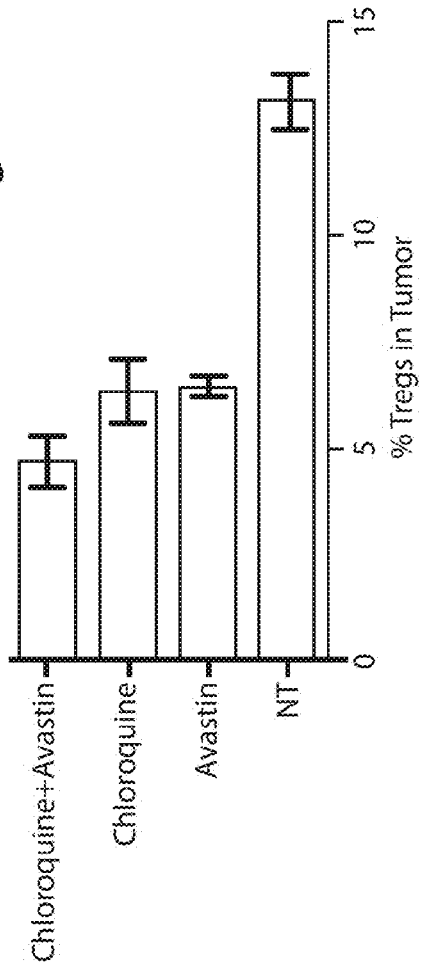
FIG. 4 is a graph showing the lower number of Treg cells in the treated animals of FIG. 1 versus the number of lymph node cells in the untreated tumor bearing animals of FIG. 1.

FIG. 3 shows the percent death in vitro using the drugs in cell culture. FIG. 4 shows the lower number of lymph node cells in the treated animals versus the number of lymph node cells in the untreated tumor bearing animals, presumably because the lymphocytes are recruited to the tumor. There are less cells in the nodes of the treated animals. The tumors of the treated animals contained lymphocytes, while the untreated animal tumors had undetectable numbers of lymphocytes. The spleens of the treated animals were very large.

The data in FIGS. 1-4 show that chloroquine and bevacizumab together are more effective than individual treatments, because the tumor sizes in vivo together are smaller. Also the in vivo tumor rate of growth is lower with both together.

Scientific Summary of the Data
Chloroquine is a lysosomatropic compound that affects the organelle known as the lysosome. The lysosome performs basic functions in the cell, including the breakdown of proteins and fatty acids for uses including fuel substrates; the lysosome is also the site where foreign antigens that have been engulfed get broken down for presentation to T lymphocytes in the immune system. In addition, in some cells, melanocytes in particular, melanin can be stored in lysosomes until the cell dies, releases the melanin that is pigmented. At that point skin cells known as keratinocytes engulf the melanosome such that when the keratinocyte dies, it becomes part of the epidermis and is colored by the melanin—hence tanning of skin.

Melanoma is a skin cancer that accounts for only 4% of skin cancer, but accounts for almost all deaths from skin cancer. Avastin is a monoclonal antibody to VEG-F (vascular epithelial growth factor) that has shown promise in clinical trials. The interpretation has been that avastin may help block the blood flow necessary to feed the growth of the tumor. Melanoma and pancreatic beta cell tumor cells were treated with avastin in vitro and observed, by using cell cycle analysis, that avastin had the effect of growth arresting the melanoma cells in $G_0$-$G_1$ phase. When we treated the cells with chloroquine and avastin, the cells underwent apoptotic death. (FIG. 3)

Figure 5:
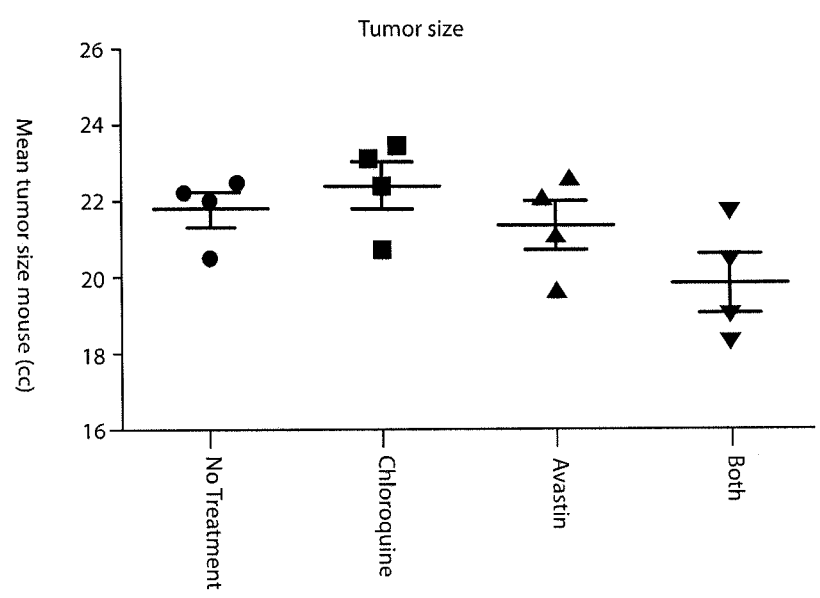
FIG. 5 shows melanoma and pancreatiC beta cell tumor cells were treated with avastin in vitro and observed, by using cell cycle analysis, that avastin had the effect of growth arresting the melanoma cells in $G_0$-$G_1$ phase.
Figure 6:
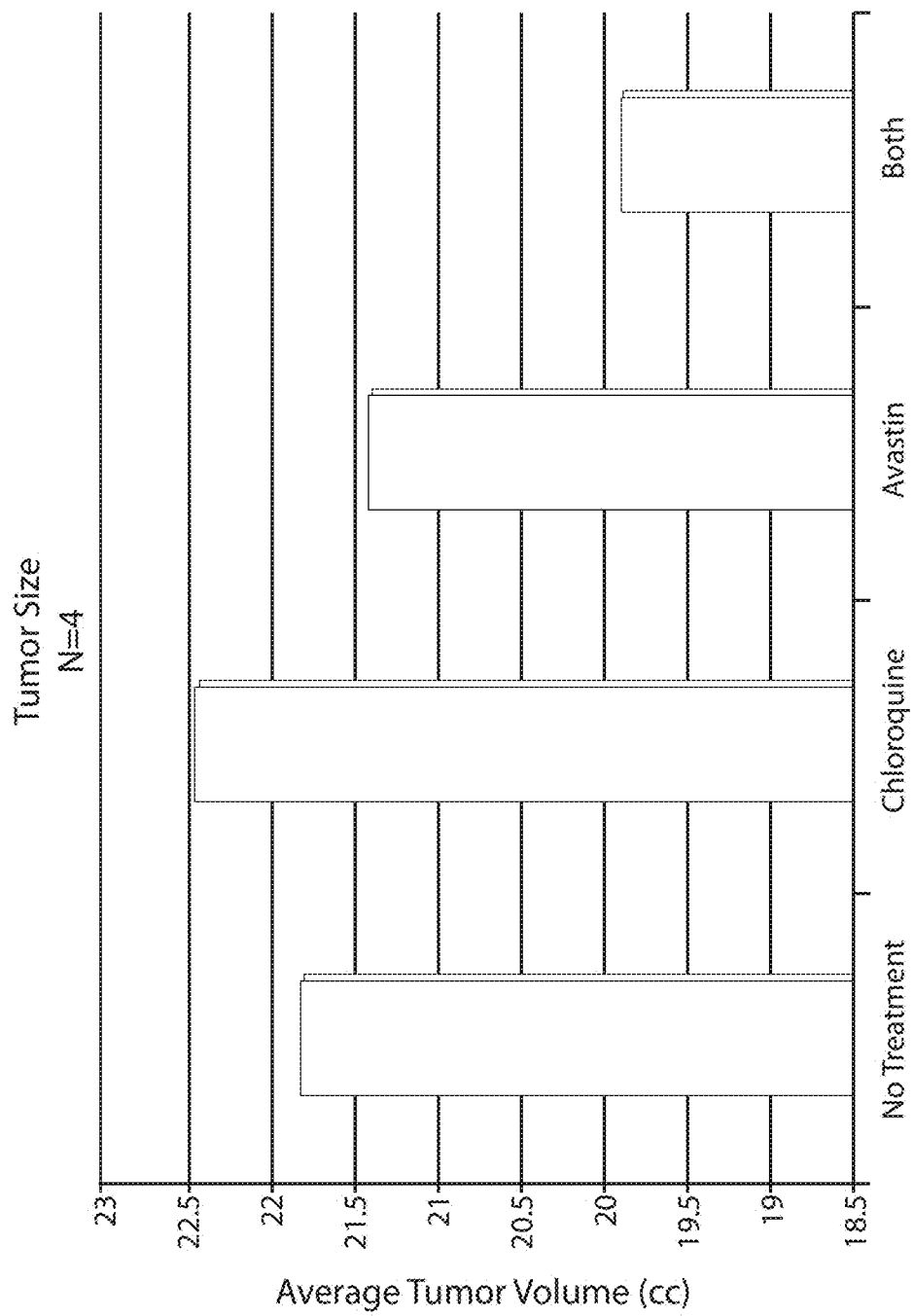
FIG. 6 shows the effects of each drug alone and combined on the tumor volume in mice, compared to control.

When the drugs chloroquine and avastin are combined, the data show that the melanoma cells are induced to die by apoptosis. (FIG. 4b) FIGS. 5-6 depict the results of the in vivo tumor measurments.

The combination of chloroquine and Avastin™ in vivo resulted in significantly smaller tumor size, as shown herein. It is believed that the distress of drug treatment alerts the immune system to danger, and anti-danger immune response (conventional T cells) diminishes the number of tumor growth-promoting cells called $CD4^+$ T regulatory cells (Tregs).

DEFINITIONS

Following are several definitions which will aid in understanding of the scope of the compounds described above and in understanding the invention. All definitions, as defined and used herein, should be understood to control over dictionary definitions, definitions in documents incorporated by reference, and/or ordinary meanings of the defined terms.

As used herein, the term "halogen," or equivalently, "halogen atom," is given its ordinary meaning as used in the field of chemistry. The halogens include fluorine, chlorine, bromine, iodine, and astatine. Preferably, the halogen atoms used in the present invention include one or more of fluorine, chlorine, bromine, or iodine. In certain embodiments of the invention, the halogen atoms found within the structure are fluorine, chlorine, and bromine; fluorine and chlorine; chlorine and bromine, or a single type of halogen atom.

As used herein, "alkyl" is given its ordinary meaning as used in the field of organic chemistry. Alkyl (i.e., aliphatic) moieties useful for practicing the invention can contain any of a wide number of carbon atoms, for example, between and 1 and 25 carbon atoms, between 1 and 20 carbon atoms, between 1 and 15 carbon atoms, between 1 and 10 carbon atoms, or between 1 and 5 carbon atoms. In some embodiments, the alkyl moiety will contain at least 1 carbon atom, at least 3 carbon atoms, at least 5 carbon atoms, or at least 10 carbon atoms; in other embodiments, the alkyl moiety will have at most 10 carbon atoms, at most 5 carbon atoms, or at most 3 carbon atoms. Typically, an alkyl moiety is a non-cyclic moiety.

The carbon atoms within the alkyl moiety may be arranged in any configuration within the alkyl moiety, for example, as a straight chain (i.e., a n-alkyl such as methyl, ethyl, propyl, butyl, pentyl, hexyl, heptyl, octyl, etc.) or a branched chain, i.e., a chain where there is at least one carbon atom that is covalently bonded to at least three carbon atoms (e.g., a t-butyl moiety, an isoalkyl moiety such as an isopropyl moiety or an isobutyl moiety, etc.). The alkyl moiety may contain only single bonds, or may contain one or more double and/or triple bonds within its structure, for example, as in an alkene, an alkyne, an alkadiene, an alkadiyne, an alkenyne, etc. In some cases, the alkyl moiety contains only carbon and hydrogen atoms; however, in other cases, the alkyl moiety may also contain one or more substituents, i.e., a non-carbon and non-hydrogen moiety may be present within the alkyl moiety. For example, in certain embodiments, the alkyl moiety can include a halogen, an alkoxy moiety (e.g., methoxy or ethoxy), an amine moiety (e.g., a primary, secondary, or tertiary amine), a carbonyl (e.g., an aldehyde and/or a ketone) or a hydroxide as a substituent. If more than substituent is present within the alkyl moiety, then the substituents may each be the same or different.

Similarly, a "cyclic" moiety, as used herein, is given its ordinary definition as used in the field of organic chemistry, i.e., a moiety structure that contains at least one ring of atoms, and may contain more than one ring of atoms. that is, a cyclic structure has at least one chain of atoms that does not have a terminal end. The chain may have, for example, three, four, five, six, or more atoms arranged to form a ring. In some embodiments, the cyclic moiety has a maximum size of at most ten atoms, at most eight atoms, or at most seven atoms. In some cases, the cyclic moiety may only include carbon and hydrogen atoms; however, in other cases, the atoms within the ring may also include, besides carbon atoms, nitrogen atoms, oxygen atoms, sulfur atoms, silicon atoms, or any other atom able to covalently bond to at least two different atoms (i.e., a "heterocyclic" moiety). If the cyclic moiety contains more than one ring, the rings may be arranged in any orientation with respect to each other, e.g., the rings may be fused (i.e., at least two rings have more than one atom in common, for example, as in bicyclic moieties, tricyclic moieties, etc.), spiro (i.e., two rings have only one atom in common), a ring may be a substituent on another ring, two or more rings may be connected through an alkyl moiety, etc. In some embodiments of the invention, one or more substituents may be present on the cyclic moiety. The substituents may be any substituent, as previously described in connection with alkyl moieties, for example, a halogen, an alkoxy, an amine, a hydroxide, or the like. In some embodiments, the substituents may also be alkyl moieties, as previously described, for example, methyl, ethyl, propyl, etc.

The cyclic moiety may be a saturated cyclic moiety (i.e., a moiety not containing any double or triple bonds, such as a cyclopentyl moiety, a cyclohexyl moiety, a cycloheptyl moiety, a cyclooctyl moiety, etc.) or an unsaturated cyclic moiety (i.e., a moiety containing at least one double or triple bond, such as a cycloalkenyl moiety, a cycloalkynyl moiety, an aromatic moiety, etc.). An "aromatic" moiety is given its ordinary meaning as used in the art, i.e., a moiety having at least one ring in which some electrons are delocalized in the ring. For instance, the aromatic moiety may include a benzene moiety, a naphthalenyl moiety, an anthracenyl moiety, a pyridinyl moiety, a furanyl moiety, etc. Similarly, a "non-aromatic" structure is a structure in which aromaticity of the cyclic moiety is not present. For example, a non-aromatic cyclic structure may be a saturated cyclic structure, a cycloalkenyl moiety such as a cyclopentenyl moiety or a cyclohexenyl moiety, a cycloalkynyl moiety such as a cyclooctynyl moiety or a cyclodecynyl moiety, etc.

Some of the compounds described herein are commercially available compounds, are derived from commercially available compounds, or are synthesized de novo using routine chemical synthetic procedures known to those of ordinary skill in the art and/or described herein.

In some embodiments, the systems and methods of the invention described herein may include homologs, analogs, derivatives, enantiomers and/or functionally equivalent compositions thereof of the compositions described herein, for example, as shown in FIG. 1. Such homologs, analogs, derivatives, enantiomers and functionally equivalent compositions thereof may be used in any of the systems and methods described herein. "Functionally equivalent" also refers to compositions capable of treatment of a subject that is wounded or exhibits symptoms of cancer (or other conditions described herein), a subject susceptible to or otherwise at increased risk for cancer, or a subject not exhibiting symptoms of cancer, but for whom it is desired to decrease the risk of cancer (e.g., a vaccination or a prophylactic treatment), etc. It will be understood that one of ordinary skill in the art will be able to manipulate the conditions in a manner to prepare such homologs, analogs, derivatives, enantiomers and functionally equivalent compositions as necessary. Homologs, analogs, derivatives, enantiomers and/or functionally equivalent compositions that are about as effective or more effective than the parent compound are also intended for use in the systems and methods of the invention. The synthesis of such compositions may be accomplished through typical chemical modification methods such as those routinely practiced by those of ordinary skill in the art.

The indefinite articles "a" and "an," as used herein in the specification and in the claims, unless clearly indicated to the contrary, should be understood to mean "one or more other."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified. Thus, as a non-limiting example, a reference to "A and/or B" can refer, in one embodiment, to A only (optionally including elements other than B); in another embodiment, to B only (optionally including elements other than A); in yet another embodiment, to both A and B (optionally including other elements); etc.

As used herein in the specification and in the claims, unless clearly indicated to the contrary, "or" should be understood to have the same meaning as "and/or" as defined above. For example, when separating items in a list, "or" and "and/or" each shall be interpreted as being inclusive, i.e., the inclusion of at least one, but also including more than one, of a number or list of elements, and, optionally, additional unlisted items. In general, the term "or" as used herein shall only be interpreted as indicating exclusive alternatives (i.e. "one or the other but not both") when preceded by terms of exclusivity, such as "only one of" or "exactly one of."

As used herein in the specification and in the claims, the phrase "at least one," in reference to a list of one or more other elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements that the phrase "at least one" refers to, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one act, the order of the acts of the method is not necessarily limited to the order in which the acts of the method are recited.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

While several embodiments of the present invention have been described and illustrated herein, those of ordinary skill in the art will readily envision a variety of other means and/or structures for performing the functions and/or obtaining the results and/or one or more other of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

REFERENCES

1. Brundtland, G. H., World Cancer Report, ed. B. W. Stewart and P. Kleihues. 2003, Lyon: International Agency for Research on Cancer, World Health Organization. 352.
2. Marrack, P. and J. Kappler, *The T cell receptor*. Science, 1987. 238: p. 1073-1079.
3. Bretscher, P. A. and M. Cohn, *A theory of self-nonself discrimination*. Science, 1970. 169: p. 1042-1049.
4. Linsley, P. S, and J. A. Ledbetter, *The role of the CD28 receptor during T cell responses to antigen*. Ann. Rev. Immunol., 1993. 11: p. 191-212.
5. Linsley, P. S., et al., *Human B7-1 (CD80) and B7-2 (CD86) bind with similar avidities but distinct kinetics to CD28 and CTLA4*. Immunity, 1994. 1: p. 793-801.
6. June, C. H., et al., *The B7 and CD28 receptor families*. Immunol. Today, 1994. 15: p. 321-330.
7. Kuchroo, V. K., et al., *B7-1 and B7-2 costimulatory molecules activate differentially the Th1/Th2 developmental pathways: application to autoimmune disease therapy*. Cell, 1995. 80: p. 707-718.
8. Lanier, L. L., et al., *CD80(B7) and CD86(B70) provide similar costimulatory signals for T cell proliferation, cytokine production, and generation of CTL*. Journal of Immunology, 1995. 154: p. 97-105.
9. Alderson, M. R., et al., *Fas transduces activation signals in normal human T lymphocytes*. J. Exp. Med., 1993. 178: p. 2231-2235.

10. Nagata, S., *Human autoimmune lymphoproliferative syndrome, a defect in the apoptosis-inducing Fas receptor: a lesson from the mouse model.* J. Human Genetics, 1998.43(1): p. 2-8.
11. Desbarats, J., et al., *Dichotomy between naïve and memory CD4+ T cell responses to Fas (CD95) engagement.* Proc. Natl. Acad. Sci. USA, 1999. 96: p. 8104-8109.
12. Desbarats, J. and M. K. Newell, *Fas engagement accelerates liver regeneration after partial hepatectomy.* Nature Medicine, 2000. 6(8): p. 920-923.
13. Pollock, B. H., et al., *Risk factors for pediatric human immunodeficiency virus-related malignancy.* JAMA, 2003.289(18): p. 2393-9.
14. Mavligit, G. M., et al., *Cell-mediated immunity to human solid tumors: in vitro detection by lymphocyte blastogenic responses to cell-associated and solubilized tumor antigens.* Natl Cancer Inst Monogr, 1973. 37: p. 167-76.
15. Whelan, M., et al., *Cancer immunotherapy: an embarrassment of riches?* Drug Discov Today, 2003.8(6): p. 253-8.
16. Martindale, D., *T Cell Triumph. Immunotherapy may have finally turned a corner. Sci Am,* 2003.288(2): p. 18-19.
17. Tsuruo, T., et al., *Molecular targeting therapy of cancer: drug resistance, apoptosis and survival signal.* Cancer Sci, 2003. 94(1): p. 15-21.
18. Kataoka, T., et al., *Expression level of c-FLIP versus Fas determines susceptibility to Fas ligand-induced cell death in murine thymoma EL-4 cells.* Exp Cell Res, 2002. 273(2): p. 256-64.
19. Sinkovics, J. G. and J. C. Horvath, *Virological and immunological connotations of apoptotic and anti-apoptotic forces in neoplasia.* Int J Oncol, 2001. 19(3): p. 473-88.
20. Green, D. R. and G. I. Evan, *A matter of life and death.* Cancer Cell, 2002. 1(1): p. 19-30.
21. Tolomeo, M. and D. Simoni, *Drug resistance and apoptosis in cancer treatment: development of new apoptosis-inducing agents active in drug resistant malignancies.* Curr Med Chem Anti-Canc Agents, 2002. 2(3): p. 387-401.
22. Landowski, T. H., et al., *Myeloma cells selected for resistance to CD95-mediated apoptosis are not cross-resistant to cytotoxic drugs: evidence for independent mechanisms of caspase activation.* Blood, 1999. 94(1): p. 265-74.
23. Carew, J. S. et al., *Autophagy.* 2007 September-October; 3(5):464-7. Epub 2007 Apr. 19

What is claimed is:

1. A method for treating cancer, comprising:
administering to a subject a therapeutically acceptable amount of an autophagy inhibitor and a VEGF receptor antagonist in an effective amount to treat the cancer, wherein the VEGF receptor antagonist is a small molecule inhibitor of a VEGFR tyrosine kinase and the autophagy inhibitor is chloroquine, and wherein the autophagy inhibitor and the VEGF receptor antagonist are administered sequentially.

2. The method of claim 1, wherein the cancer is melanoma.

3. The method of claim 1, wherein the cancer is a multidrug resistant cancer.

4. The method of claim 1, wherein the autophagy inhibitor is hydroxychloroquine.

5. The method of any one of claims 1, 3, and 4, wherein the cancer is breast cancer.

6. The method of any one of claims 1, 3, and 4, wherein the cancer is ovarian cancer.

7. The method of any one of claims 1, 3, and 4, wherein the cancer is lung cancer.

8. The method of any one of claims 1, 3, and 4, wherein the cancer is glioblastoma.

* * * * *